(12) United States Patent
Flohr et al.

(10) Patent No.: US 7,371,748 B2
(45) Date of Patent: May 13, 2008

(54) BENZOTHIAZOLE DERIVATIVES

(75) Inventors: Alexander Flohr, Basel (CH); Roland Jakob-Roetne, Inzlingen (DE); Roger David Norcross, Rheinfelden (CH); Claus Riemer, Freiburg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 501 days.

(21) Appl. No.: 10/847,558

(22) Filed: May 17, 2004

(65) Prior Publication Data

US 2004/0235915 A1    Nov. 25, 2004

(30) Foreign Application Priority Data

May 19, 2003   (EP) .................................. 03011039

(51) Int. Cl.
*C07D 413/14* (2006.01)
*C07D 417/02* (2006.01)
*A61K 31/4436* (2006.01)
*A61K 31/5377* (2006.01)

(52) U.S. Cl. ................... 514/233.8; 514/318; 514/321; 514/338; 514/367; 544/130; 544/131; 544/135; 546/193; 546/198; 546/270.1; 548/163

(58) Field of Classification Search ................ 514/367; 548/163
See application file for complete search history.

(56) References Cited

U.S. PATENT DOCUMENTS 6,734,179 B2 * 5/2004 Flohr et al. ............... 514/233.8

6,992,083 B2 * 1/2006 Norcross ................. 514/233.8

FOREIGN PATENT DOCUMENTS

| WO | WO 01/97786 | 12/2001 |
| WO | WO 03/045385 | 6/2003 |
| WO | WO 03/049741 | 6/2003 |
| WO | WO 03/053961 | 7/2003 |

* cited by examiner

*Primary Examiner*—Kamal A. Saeed
(74) *Attorney, Agent, or Firm*—George W. Johnston; Patricia S. Rocha-Tramaloni; Gene J. Yao

(57) ABSTRACT

This invention relates to compounds of formula I

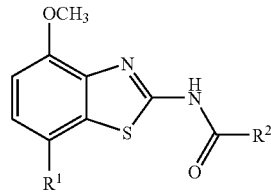

wherein
$R^1$ and $R^2$ are defined herein, or a pharmaceutically acceptable salt thereof.

It has been found that the compounds of formula I are adenosine receptor ligands with good affinity to the $A_{2A}$-receptor and a high selectivity to the $A_1$- and $A_3$ receptors. These compounds are useful, inter alia, in treatment of Alzheimer's disease, depression, Parkinson's disease and ADHD.

16 Claims, No Drawings

BENZOTHIAZOLE DERIVATIVES

FIELD OF THE INVENTION

The present invention relates to a novel adenosine receptor ligand of formula I

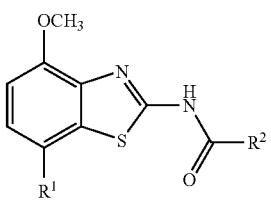

wherein $R^1$ and $R^2$ are described hereinbelow. These ligands (compounds) have a good affinity to the $A_{2A}$-receptor and a high selectivity to the $A_1$- and $A_3$ receptors. These compounds are useful, inter alia, in treatment of Alzheimer's disease, depression, Parkinson's disease and ADHD.

BACKGROUND OF THE INVENTION

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzym A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterized by the adenylate cyclase effector system, which utilizes cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326-328 amino acids) was cloned from various species (canine, human, rat, dog, chick, bovine, guinea-pig) with 90-95% sequence identify among the mammalian species. The $A_{2A}$ receptor (409-412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317-320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The action of both subtypes is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioral state and (patho) physiological conditions. Under conditions of increased demand and decreased availability of energy (such as hypoxia, hypoglycemia, and/or excessive neuronal activity), adenosine provides a powerful protective feedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents.

Adenosine antagonists stimulate the activity of the CNS and have proven to be effective as cognition enhancers. Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyper-activity disorder).

An important role for adenosine in the cardiovascular system is as a cardioprotective agent. Levels of endogenous adenosine increase in response to ischaemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_{2a}$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricula arrhytmias.

Adenosine modulates many aspects of renal function, including renin release, glomerular filtration rate and renal blood flow. Compounds which antagonise the renal affects of adenosine have potential as renal protective agents. Furthermore, adenosine $A_3$ and/or $A_{2B}$ antagonists may be useful in the treatment of asthma and other allergic responses or and in the treatment of diabetes mellitus and obesity.

Numerous documents describe the current knowledge on adenosine receptors. These include Bioorganic & Medicinal Chemistry, 6, (1998), 619-641, Bioorganic & Medicinal Chemistry, 6, (1998), 707-719, J. Med. Chem., (1998), 41, 2835-2845, J. Med. Chem., (1998), 41, 3186-3201, J. Med. Chem., (1998), 41, 2126-2133, J. Med. Chem., (1999), 42,706-721, J. Med. Chem., (1996), 39,1164-1171, Arch. Pharm. Med. Chem., 332,39-41, (1999), Am. J. Physiol., 276, H1113-1116, (1999) and Naunyn Schmied, Arch. Pharmacol. 362, 375-381, (2000).

SUMMARY OF THE INVENTION

An aspect of the present invention is directed to the compounds of formula I

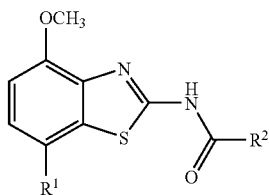

wherein,
$R^1$ is selected from 1,4-dioxepanyl and tetrahydropyran-4-yl;
$R^2$ is selected from
—N(R)—$(CH_2)_n$-5 membered non aromatic heterocycle,
—N(R)—$(CH_2)_n$-5 membered non aromatic heterocycle substituted by one or two substituents selected from lower alkyl, $(CH_2)_n$—OH and —$NR_2$,
—N(R)—$(CH_2)_n$-6 membered non aromatic heterocycle,
—N(R)—$(CH_2)_n$-6 membered non aromatic heterocycle substituted by one or two substituents selected from lower alkyl, $(CH_2)_n$—OH and —$NR_2$,
—$(CH_2)_n$-5 membered non aromatic heterocycle,
—$(CH_2)_n$-5 membered non aromatic heterocycle substituted by one or two substituents selected from —$(CH_2)_n$—OH, lower alkyl and lower alkoxy,
—$(CH_2)_n$-6 membered non aromatic heterocycle,
—$(CH_2)_n$-6 membered non aromatic heterocycle substituted by one or two substituents selected from —$(CH_2)_n$—OH, lower alkyl and lower alkoxy
—$(CH_2)_n$-5 membered aromatic heterocycle,
—$(CH_2)_n$-5 membered aromatic heterocycle substituted by one or two substituents selected from the group consisting of lower alkyl, lower alkoxy, halogen, halogen-lower alkyl, —$CH_2N(R)(CH_2)_2OCH_3$, —N(R)$(CH_2)_2OCH_3$, —$CH_2$-morpholinyl and —$CH_2$-pyrrolidinyl,
—$(CH_2)_n$-6 membered aromatic heterocycle,
—$(CH_2)_n$-6 membered aromatic heterocycle substituted by one or two substituents selected from the group consisting of lower alkyl, lower alkoxy, halogen, halogen-lower alkyl, —$CH_2N(R)(CH_2)_2OCH_3$, —N(R)$(CH_2)_2OCH_3$, —$CH_2$-morpholinyl and —$(CH_2)_n$-pyrrolidinyl,
$(CH_2)_n$-cycloalkyl,
$(CH_2)_n$-cycloalkyl substituted by hydroxy,
—N(R)—$(CH_2)_n$-cycloalkyl,
—N(R)—$(CH_2)_n$-cycloalkyl substituted by a group selected from hydroxy and lower alkyl,
—N(R)—$(CH_2)_n$-phenyl,
phenyl,
phenyl substituted by one or two substituents selected from the group consisting of lower alkoxy, halogen, halogen-lower alkyl, lower alkyl, —$CH_2$-pyrrolidin-1-yl, —$CH_2$-morpholinyl, —$CH_2N(R)(CH_2)_2OCH_3$ and —$CH_2$—N(R)C(O)-lower alkyl,
1,4-dioxa-8-aza-spiro[4,5]decane,
2-oxa-5-aza-bicyclo[2.2.1]heptane,
1-oxa-8-aza-spiro[4,5]decane,
—N(R)—$(CH_2)_n$-7-oxa-bicyclo[2.2.1]hept-2-yl, and
2-aza-bicyclo[2.2.2]decane;
R is selected from hydrogen or lower alkyl; and
n is 0 or 1;
or a pharmaceutically acceptable salt thereof.

Other embodiments of this invention are directed to methods of manufacture of compounds of formula I, pharmaceutical compositions containing a compound of formula I, and a pharmaceutically acceptable salt thereof, as well as a method of controlling or prevention of illnesses based on the modulation of the adenosine system, such as Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse comprising administering to a patient a therapeutically effective amount of a compound of formula I or a pharmaceutically acceptable salt thereof.

Furthermore, compounds of the present invention are useful as sedatives, muscle relaxants, antipsychotics, antiepileptics, anticonvulsants and cardioprotective agents for disorders such as coronary artery disease and heart failure. Preferred indications in accordance with the present invention are those, that depend on the $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION OF THE INVENTION

As used herein, the term "lower alkyl" refers to a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1-4 carbon atoms.

The term "halogen" refers to chlorine, iodine, fluorine and bromine.

The term "lower alkoxy" refers to a group wherein the alkyl residues is as defined above, and which is attached to the rest of the molecule via an oxygen atom.

The term "cycloalkyl" refers to a saturated carbocyclic group, containing 3-7 carbon atoms.

The term "5-or 6 membered non aromatic heterocycle" refers to rings like morpholin, piperazin, piperidin, tetrahydropyran or tetrahydrofuran.

The term "5-or 6 membered aromatic heterocycle" refers to rings like thiophene, imidazole, pyrazole or pyridine.

The term "pharmaceutically acceptable salts" refers to salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

The term "therapeutically effective amount" refers to an amount of at least one compound of formula I, or a pharmaceutically acceptable salt thereof, that modulates adenosine.

In one embodiment, this invention relates to a compound of the formula I

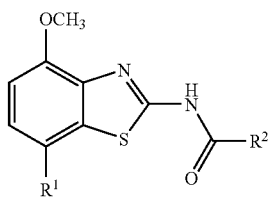

I wherein
$R^1$ is 1,4-dioxepanyl;
$R^2$ is selected from
—N(R)—$(CH_2)_n$-5 membered non aromatic heterocycle,
—N(R)—$(CH_2)_n$-5 membered non aromatic heterocycle substituted by one or two substituents selected from lower alkyl, $(CH_2)_n$—OH and —$NR_2$,
—N(R)—$(CH_2)_n$-6 membered non aromatic heterocycle,
—N(R)—$(CH_2)_n$-6 membered non aromatic heterocycle substituted by one or two substituents selected from lower alkyl, $(CH_2)_n$—OH and —$NR_2$,
—$(CH_2)_n$-5 membered non aromatic heterocycle,
—$(CH_2)_n$-5 membered non aromatic heterocycle substituted by one or two substituents selected from —$(CH_2)_n$—OH, lower alkyl and lower alkoxy,
—$(CH_2)_n$-6 membered non aromatic heterocycle,
—$(CH_2)_n$-6 membered non aromatic heterocycle substituted by one or two substituents selected from —$(CH_2)_n$—OH, lower alkyl and lower alkoxy
—$(CH_2)_n$-5 membered aromatic heterocycle,
—$(CH_2)_n$-5 membered aromatic heterocycle substituted by one or two substituents selected from the group consisting of lower alkyl, lower alkoxy, halogen, halogen-lower alkyl, —$CH_2N(R)(CH_2)_2OCH_3$, —N(R)$(CH_2)_2OCH_3$, —$CH_2$-morpholinyl and —$CH_2$-pyrrolidinyl,
—$(CH_2)_n$-6 membered aromatic heterocycle,
—$(CH_2)_n$-6 membered aromatic heterocycle substituted by one or two substituents selected from the group consisting of lower alkyl, lower alkoxy, halogen, halogen-lower alkyl, —$CH_2N(R)(CH_2)_2OCH_3$, —N(R)$(CH_2)_2OCH_3$, —$CH_2$-morpholinyl and —$(CH_2)_n$-pyrrolidinyl,
$(CH_2)_n$-cycloalkyl,
$(CH_2)_n$-cycloalkyl substituted by hydroxy,
—N(R)—$(CH_2)_n$-cycloalkyl,
—N(R)—$(CH_2)_n$-cycloalkyl substituted by a substituent selected from hydroxy and lower alkyl,
—N(R)—$(CH_2)_n$-phenyl,
phenyl,
phenyl substituted by one or two substituents selected from the group consisting of lower alkoxy, halogen, halogen-lower alkyl, lower alkyl, —$CH_2$-pyrrolidin-1-yl, —$CH_2$-morpholinyl, —$CH_2N(R)(CH_2)_2OCH_3$ and —$CH_2$—N(R)C(O)-lower alkyl,
1,4-dioxa-8-aza-spiro[4,5]decane,
2-oxa-5-aza-bicyclo[2.2.1]heptane,
1-oxa-8-aza-spiro[4,5]decane,
—N(R)—$(CH_2)_n$-7-oxa-bicyclo[2.2.1]hept-2-yl, and
2-aza-bicyclo[2.2.2]decane;
R is selected from hydrogen or lower alkyl; and
n is 0 or 1;

or a pharmaceutically acceptable salt thereof.

In an preferred embodiment, this invention is related to a compound of formula I

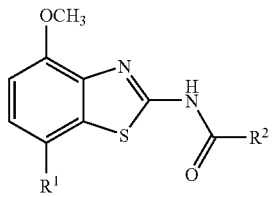

I wherein
$R^1$ is 1,4-dioxepanyl;
$R^2$ is selected from
—N(R)—$(CH_2)_n$-6 membered non aromatic heterocycle,
—N(R)—$(CH_2)_n$-6 membered non aromatic heterocycle substituted by one or two substituents selected from lower alkyl and $(CH_2)_n$—OH,
—$(CH_2)_n$-5 membered non aromatic heterocycle,
—$(CH_2)_n$-6 membered non aromatic heterocycle,
—$(CH_2)_n$-6 membered non aromatic heterocycle substituted by —$(CH_2)_n$—OH
—$(CH_2)_n$-5 membered aromatic heterocycle substituted by one or two substituents selected from the group consisting of lower alkyl,
—$(CH_2)_n$-6 membered aromatic heterocycle,
—$(CH_2)_n$-6 membered aromatic heterocycle substituted by one or two substituents selected from the group consisting of lower alkoxy, halogen, —$CH_2N(R)(CH_2)_2OCH_3$, and —$(CH_2)_n$-pyrrolidinyl,
$(CH_2)_n$-cycloalkyl,
—N(R)-cycloalkyl substituted by hydroxy,
phenyl substituted by one or two substituents selected from the group consisting of halogen, lower alkyl, —$CH_2$-pyrrolidin-1-yl, —$CH_2N(R)(CH_2)_2OCH_3$ and —$CH_2$—N(R)C(O)-lower alkyl,
1,4-dioxa-8-aza-spiro[4,5]decane,
2-oxa-5-aza-bicyclo[2.2.1]heptane, and
1-oxa-8-aza-spiro[4,5]decane;
R is selected from hydrogen or lower allyl; and
n is 0 or 1;

or a pharmaceutically acceptable salt thereof.

In another embodiment, this invention is related to a compound of formula I

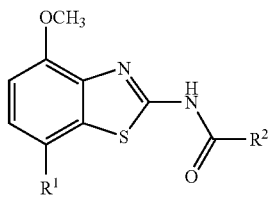

wherein
R¹ is tetrahydropyran-4-yl;
R² is selected from
—N(R)—(CH₂)ₙ-5 membered non aromatic heterocycle,
—N(R)—(CH₂)ₙ-5 membered non aromatic heterocycle substituted by one or two substituents selected from lower alkyl, (CH₂)ₙ—OH and —NR₂,
—N(R)—(CH₂)ₙ-6 membered non aromatic heterocycle,
—N(R)—(CH₂)ₙ-6 membered non aromatic heterocycle substituted by one or two substituents selected from lower alkyl, (CH₂)ₙ—OH and —NR₂,
—(CH₂)ₙ-5 membered non aromatic heterocycle,
—(CH₂)ₙ-5 membered non aromatic heterocycle substituted by one or two substituents selected from —(CH₂)ₙ—OH, lower alkyl and lower alkoxy,
—(CH₂)ₙ-6 membered non aromatic heterocycle,
—(CH₂)ₙ-6 membered non aromatic heterocycle substituted by one or two substituents selected from —(CH₂)ₙ—OH, lower alkyl and lower alkoxy
—(CH₂)ₙ-5 membered aromatic heterocycle,
—(CH₂)ₙ-5 membered aromatic heterocycle substituted by one or two substituents selected from the group consisting of lower alkyl, lower alkoxy, halogen, halogen-lower alkyl, —CH₂N(R)(CH₂)₂OCH₃, —N(R)(CH₂)₂OCH₃, —CH₂-morpholinyl and —CH₂-pyrrolidinyl,
—(CH₂)ₙ-6 membered aromatic heterocycle,
—(CH₂)ₙ-6 membered aromatic heterocycle substituted by one or two substituents selected from the group consisting of lower alkyl, lower alkoxy, halogen, halogen-lower alkyl, —CH₂N(R)(CH₂)₂OCH₃, —N(R)(CH₂)₂OCH₃, —CH₂-morpholinyl and —(CH₂)ₙ-pyrrolidinyl,
(CH₂)ₙ-cycloalkyl,
(CH₂)ₙ-cycloalkyl substituted by hydroxy,
—N(R)—(CH₂)ₙ-cycloalkyl,
—N(R)—(CH₂)ₙ-cycloalkyl substituted by a group selected from hydroxy and lower alkyl,
—N(R)—(CH₂)ₙ-phenyl,
phenyl,
phenyl substituted by one or two substituents selected from the group consisting of lower alkoxy, halogen, halogen-lower alkyl, lower alkyl, —CH₂-pyrrolidin-1-yl, —CH₂-morpholinyl, —CH₂N(R)(CH₂)₂OCH₃ and —CH₂—N(R)C(O)-lower alkyl,
1,4-dioxa-8-aza-spiro[4,5]decane,
2-oxa-5-aza-bicyclo[2.2.1]heptane,
1-oxa-8-aza-spiro[4,5]decane,
—N(R)—(CH₂)ₙ-7-oxa-bicyclo[2.2.1]hept-2-yl, and
2-aza-bicyclo[2.2.2]decane;
R is selected from hydrogen or lower alkyl; and
n is 0 or 1;

or a pharmaceutically acceptable salt thereof.

In a preferred embodiment, this invention is directed to a compounds of formula I

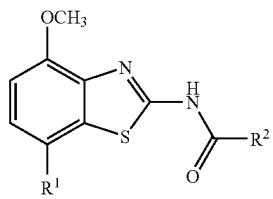

wherein
R¹ is tetrahydropyran-4-yl;
R² is selected from
—N(R)—(CH₂)ₙ-5 membered non aromatic heterocycle,
—N(R)—(CH₂)ₙ-6 membered non aromatic heterocycle,
—N(R)—(CH₂)ₙ-6 membered non aromatic heterocycle substituted by one or two substituents selected from lower alkyl and —NR₂,
—(CH₂)ₙ-5 membered non aromatic heterocycle,
—(CH₂)ₙ-6 membered non aromatic heterocycle,
—(CH₂)ₙ-6 membered non aromatic heterocycle substituted by one or two substituents selected from —(CH₂)ₙ—OH and lower alkyl,
—(CH₂)ₙ-6 membered aromatic heterocycle substituted by one or two substituents selected from —CH₂N(R)(CH₂)₂OCH₃ and —CH₂-morpholinyl,
(CH₂)ₙ-cycloalkyl substituted by hydroxy,
—N(R)—(CH₂)ₙ-cycloalkyl substituted by a group selected from hydroxy and lower alkyl,
—N(R)—(CH₂)ₙ-phenyl,
1,4-dioxa-8-aza-spiro[4,5]decane,
2-oxa-5-aza-bicyclo[2.2.1]heptane,
—N(R)—(CH₂)ₙ-7-oxa-bicyclo[2.2.1]hept-2-yl, and
2-aza-bicyclo[2.2.2]decane;
R is selected from hydrogen or lower alkyl; and
n is 0 or 1;

or a pharmaceutically acceptable salt thereof.
Preferred compounds of the present application are compounds of formula I,
wherein
R¹ is 1,4-dioxepan-6-yl; and
R² is selected from
—N(R)—(CH₂)ₙ-6 membered non aromatic heterocycle,
—N(R)—(CH₂)ₙ-6 membered non aromatic heterocycle substituted by one or two substituents selected from lower alkyl and (CH₂)ₙ—OH,
—(CH₂)ₙ-5 membered non aromatic heterocycle,
—(CH₂)ₙ-6 membered non aromatic heterocycle,
—(CH₂)ₙ-6 membered non aromatic heterocycle substituted by —(CH₂)ₙ—OH
—(CH₂)ₙ-5 membered aromatic heterocycle substituted by one or two substituents selected from the group consisting of lower alkyl,
—(CH₂)ₙ-6 membered aromatic heterocycle,
—(CH₂)ₙ-6 membered aromatic heterocycle substituted by one or two substituents selected from the group consisting of lower alkoxy, halogen, —CH₂N(R)(CH₂)₂OCH₃, and —(CH₂)ₙ-pyrrolidinyl,
(CH₂)ₙ-cycloalkyl,
—N(R)-cycloalkyl substituted by hydroxy,
phenyl substituted by one or two substituents selected from the group consisting of halogen, lower alkyl, —CH$_2$-pyrrolidin-1-yl, —CH$_2$N(R)(CH$_2$)$_2$OCH$_3$ and —CH$_2$—N(R)C(O)-lower alkyl,
1,4-dioxa-8-aza-spiro[4,5]decane,
2-oxa-5-aza-bicyclo[2.2.1]heptane, and
1-oxa-8-aza-spiro[4,5]decane,
R is selected from hydrogen or lower alkyl; and
n is 0 or 1;

or a pharmaceutically acceptable salt thereof.

In a preferred embodiment of the compound of formula I, when R$^1$ is 1,4-dioxepan-6-yl, R$^2$ is —N(R)—(CH$_2$)$_n$-6 membered non aromatic heterocycle, R is selected from hydrogen or lower alkyl, and n is 0 or 1.

In another preferred embodiment of the compound of formula I, when R$^1$ is 1,4-dioxepan-6-yl, R$^2$ is —N(R)—(CH$_2$)$_n$-6 membered non aromatic heterocycle substituted by one or two substituents selected from lower alkyl and (CH$_2$)$_n$—OH, R is selected from hydrogen or lower alkyl, and n is 0 or 1.

In another preferred embodiment of the compound of formula I, when R$^1$ is 1,4-dioxepan-6-yl, R$^2$ is —(CH$_2$)$_n$-5 membered non aromatic heterocycle, and n is 0 or 1.

In another preferred embodiment of the compound of formula I, when R$^1$ is 1,4-dioxepan-6-yl, R$^2$ is —(CH$_2$)$_n$-6 membered non aromatic heterocycle, and n is 0 or 1.

In another preferred embodiment of the compound of formula I, when R$^1$ is 1,4-dioxepan-6-yl, R$^2$ is —(CH$_2$)$_n$-6 membered non aromatic heterocycle substituted by —(CH$_2$)$_n$—OH, and n is 0 or 1.

In another preferred embodiment of the compound of formula I, when R$^1$ is 1,4-dioxepan-6-yl, R$^2$ is —(CH$_2$)$_n$-5 membered aromatic heterocycle substituted by one or two substituents selected from the group consisting of lower alkyl, and n is 0 or 1.

In another preferred embodiment of the compound of formula I, when R$^1$ is 1,4-dioxepan-6-yl, R$^2$ is —(CH$_2$)$_n$-6 membered aromatic heterocycle, and n is 0 or 1.

In another preferred embodiment of the compound of formula I, when R$^1$ is 1,4-dioxepan-6-yl, R$^2$ is —(CH$_2$)$_n$-6 membered aromatic heterocycle substituted by one or two substituents selected from the group consisting of lower alkoxy, halogen, —CH$_2$N(R)(CH$_2$)$_2$OCH$_3$, and —(CH$_2$)$_n$-pyrrolidinyl, R is selected from hydrogen or lower alkyl, and n is 0 or 1.

In another preferred embodiment of the compound of formula I, when R$^1$ is 1,4-dioxepan-6-yl, R$^2$ is (CH$_2$)$_n$-cycloalkyl, and n is 0 or 1.

In another preferred embodiment of the compound of formula I, when R$^1$ is 1,4-dioxepan-6-yl, R$^2$ is —N(R)-cycloalkyl substituted by hydroxy, and R is selected from hydrogen or lower alkyl.

In another preferred embodiment of the compound of formula I, when R$^1$ is 1,4-dioxepan-6-yl, R$^2$ is phenyl substituted by one or two substituents selected from the group consisting of halogen, lower alkyl, —CH$_2$-pyrrolidin-1-yl, —CH$_2$N(R)(CH$_2$)$_2$OCH$_3$ and —CH$_2$—N(R)C(O)-lower alkyl, and R is selected from hydrogen or lower alkyl.

In another preferred embodiment of the compound of formula I, when R$^1$ is 1,4-dioxepan-6-yl, R$^2$ is phenyl substituted by one or two substituents selected from the group consisting of halogen, lower alkyl, —CH$_2$-pyrrolidin-1-yl, —CH$_2$N(R)(CH$_2$)$_2$OCH$_3$ and —CH$_2$—N(R)C(O)-lower alkyl, and R is selected from hydrogen or lower alkyl.

In another preferred embodiment of the compound of formula I, when R$^1$ is 1,4-dioxepan-6-yl, R$^2$ is 1,4-dioxa-8-aza-spiro[4,5]decane.

In another preferred embodiment of the compound of formula I, when R$^1$ is 1,4-dioxepan-6-yl, R$^2$ is 2-oxa-5-aza-bicyclo[2.2.1]heptane.

In another preferred embodiment of the compound of formula I, when R$^1$ is 1,4-dioxepan-6-yl, R$^2$ is 1-oxa-8-aza-spiro[4,5]decane.

The following are some preferred compounds of formula I wherein R$^1$ is 1,4-dioxepan-6-yl:
morpholine-4-carboxylic acid (7-[1,4]dioxepan-6-yl-4-methoxy-benzothiazol-2-yl)-amide,
piperidine-1-carboxylic acid (7-[1,4]dioxepan-6-yl-4-methoxy-benzothiazol-2-yl)-amide,
1-cyclohexyl-3-(7-[1,4]dioxepan-6-yl-4-methoxy-benzothiazol-2-yl)-71-methyl-urea,
4-hydroxymethyl-piperidine-1-carboxylic acid (7-[1,4]dioxepan-6-yl-4-methoxy-benzothiazol-2-yl)-amide,
3-(7-[1,4]dioxepan-6-yl-4-methoxy-benzothiazol-2-yl)-1-methyl-1-(1-methyl-piperidin-4-yl)-urea,
1,4-dioxa-8-aza-spiro[4.5]decane-8-carboxylic acid (7-[1,4]dioxepan-6-yl-4-methoxy-benzothiazol-2-yl)-amide,
4-hydroxy-piperidine-1-carboxylic acid (7-[1,4]dioxepan-6-yl-4-methoxy-benzothiazol-2-yl)-amide,
5-methyl-thiophene-2-carboxylic acid (7-[1,4]dioxepan-6-yl-4-methoxy-benzothiazol-2-yl)-amide,
N-(7-[1,4]dioxepan-6-yl-4-methoxy-benzothiazol-2-yl)-4-methoxy-benzamide,
N-(7-[1,4]dioxepan-6-yl-4-methoxy-benzothiazol-2-yl)-4-fluoro-benzamide,
cyclohexanecarboxylic acid (7-[1,4]dioxepan-6-yl-4-methoxy-benzothiazol-2-yl)-amide,
N-(7-[1,4]dioxepan-6-yl-4-methoxy-benzothiazol-2-yl)-2-(tetrahydro-pyran-4-yl)-acetamide,
(R)-tetrahydro-furan-2-carboxylic acid (7-[1,4]dioxepan-6-yl-4-methoxy-benzothiazol-2-yl)-amide,
3-methyl-3H-imidazole-4-carboxylic acid (7-[1,4]dioxepan-6-yl-4-methoxy-benzothiazol-2-yl)-amide,
N-(7-[1,4]dioxepan-6-yl-4-methoxy-benzothiazol-2-yl)-isonicotinamide,
N-(7-[1,4]dioxepan-6-yl-4-methoxy-benzothiazol-2-yl)-2-methoxy-isonicotinamide,
trans 1-(4-hydroxy-cyclohexyl)-3-(4-methoxy-7-[1,4]dioxepan-6-yl-benzothiazol-2-yl)-1-methyl-urea,
(1S,4S)-2oxa-5-aza-bicyclo[2.2.1]heptane-5-carboxylic acid (7-[1,4]dioxepan-6-yl-4-methoxy-benzothiazol-2-yl)-amide,
4-methoxy-piperidine-1-carboxylic acid (7-[1,4]dioxepan-6-yl-4-methoxy-benzothiazol-2-yl)-amide,
4-chloromethyl-N-(7-[1,4]dioxepan-6-yl-4-methoxy-benzothiazol-2-yl)-benzamide,
1-methyl-1H-pyrazole-4-carboxylic acid (7-[1,4]dioxepan-6-yl-4-methoxy-benzothiazol-2-yl)-amide,
N-(7-[1,4]dioxepan-6-yl-4-methoxy-benzothiazol-2-yl)-4-[(methyl-propionyl-amino)-methyl]-benzamide and
N-(7-[1,4]dioxepan-6-yl-4-methoxy-benzothiazol-2-yl)-2-pyrrolidin-1-yl-isonicotinamide.

Preferred are further compounds of formula I, wherein R$^1$ is tetrahydropyran-4-yl; and
R$^2$ is selected from
—N(R)—(CH$_2$)$_n$-5 membered non aromatic heterocycle,
—N(R)—(CH$_2$)$_n$-6 membered non aromatic heterocycle,
—N(R)—(CH$_2$)$_n$-6 membered non aromatic heterocycle substituted by one or two substituents selected from lower alkyl and —NR$_2$,
—(CH$_2$)$_n$-5 membered non aromatic heterocycle,
—(CH$_2$)$_n$-6 membered non aromatic heterocycle, —(CH$_2$)$_n$-6 membered non aromatic heterocycle substituted by one or two substituents selected from —(CH$_2$)$_n$—OH and lower alkyl, —(CH$_2$)$_n$-6 membered aromatic heterocycle substituted by one or two substituents selected from —CH$_2$N(R)(CH$_2$)$_2$OCH$_3$ and —CH$_2$-morpholinyl, (CH$_2$)$_n$-cycloalkyl substituted by hydroxy, —N(R)—(CH$_2$)$_n$-cycloalkyl substituted by a group selected from hydroxy and lower alkyl, —N(R)—(CH$_2$)$_n$-phenyl, 1,4-dioxa-8-aza-spiro[4,5]decane, 2-oxa-5-aza-bicyclo[2.2.1]heptane, —N(R)—(CH$_2$)$_n$-7-oxa-bicyclo[2.2.1]hept-2-yl, and 2-aza-bicyclo[2.2.2]decane, R is selected from hydrogen or lower alkyl; and n is 0 or 1;

or a pharmaceutically acceptable salt thereof.

In a preferred embodiment of the compound of formula I, when R$^1$ is tetrahydropyran-4-yl, R$^2$ is —N(R)—(CH$_2$)$_n$-5 membered non aromatic heterocycle, R is selected from hydrogen or lower alkyl, and n is 0 or 1.

In another preferred embodiment of the compound of formula I, when R$^1$ is tetrahydropyran-4-yl, R$^2$ is —N(R)—(CH$_2$)$_n$-6 membered non aromatic heterocycle, R is selected from hydrogen or lower alkyl, and n is 0 or 1.

In another preferred embodiment of the compound of formula I, when R$^1$ is tetrahydropyran-4-yl, R$^2$ is —N(R)—(CH$_2$)$_n$-6 membered non aromatic heterocycle substituted by one or two substituents selected from lower alkyl and —NR$_2$, R is selected from hydrogen or lower alkyl, and n is 0 or 1.

In another preferred embodiment of the compound of formula I, when R$^1$ is tetrahydropyran-4-yl, R$^2$ is —(CH$_2$)$_n$-5 membered non aromatic heterocycle, and n is 0 or 1.

In another preferred embodiment of the compound of formula I, when R$^1$ is tetrahydropyran-4-yl, R$^2$ is —(CH$_2$)$_n$-6 membered non aromatic heterocycle, and n is 0 or 1.

In another preferred embodiment of the compound of formula I, when R$^1$ is tetrahydropyran-4-yl, R$^2$ is —(CH$_2$)$_n$-6 membered non aromatic heterocycle substituted by one or two substituents selected from —(CH$_2$)$_n$—OH and lower alkyl, and n is 0 or 1.

In another preferred embodiment of the compound of formula I, when R$^1$ is tetrahydropyran-4-yl, R$^2$ is —(CH$_2$)$_n$-6 membered aromatic heterocycle substituted by one or two substituents selected from —CH$_2$N(R)(CH$_2$)$_2$OCH$_3$ and —CH$_2$-morpholinyl, R is selected from hydrogen or lower alkyl, and n is 0 or 1.

In another preferred embodiment of the compound of formula I, when R$^1$ is tetrahydropyran-4-yl, R$^2$ is (CH$_2$)$_n$-cycloalkyl substituted by hydroxy, and n is 0 or 1.

In another preferred embodiment of the compound of formula I, when R$^1$ is tetrahydropyran-4-yl, R$^2$ is —N(R)—(CH$_2$)$_n$-cycloalkyl substituted by a group selected from hydroxy and lower alkyl, R is selected from hydrogen or lower alkyl, and n is 0 or 1.

In another preferred embodiment of the compound of formula I, when R$^1$ is tetrahydropyran-4-yl, R$^2$ is —N(R)—(CH$_2$)$_n$-phenyl, R is selected from hydrogen or lower alkyl, and n is 0 or 1.

In another preferred embodiment of the compound of formula I, when R$^1$ is tetrahydropyran-4-yl, R$^2$ is 1,4-dioxa-8-aza-spiro[4,5]decane.

In another preferred embodiment of the compound of formula I, when R$^1$ is tetrahydropyran-4-yl, R$^2$ is 2-oxa-5-aza-bicyclo[2.2.1]heptane.

In another preferred embodiment of the compound of formula I, when R$^1$ is tetrahydropyran-4-yl, R$^2$ is —N(R)—(CH$_2$)$_n$-7-oxa-bicyclo[2.2.1]hept-2-yl.

In another preferred embodiment of the compound of formula I, when R$^1$ is tetrahydropyran-4-yl, R$^2$ is 2-aza-bicyclo[2.2.2]decane.

The following are some preferred compounds of formula I wherein R$^1$ is tetrahydropyran-4-yl:

3-[4-methoxy-7-(tetrahydro-pyran-4-yl)-benzothiazol-2-yl]-1-methyl-1-(1-methyl-piperidin-4-yl)-urea, trans-1-(4-hydroxy-cyclohexyl)-3-[4-methoxy-7-(tetrahydro-pyran-4-yl)-benzothiazol-2-yl]-1-methyl-urea, cis-1-(4-hydroxy-cyclohexyl)-3-[4-methoxy-7-(tetrahydro-pyran-4-yl)-benzothiazol-2-yl]-1-methyl-urea, 1-(4-cis-hydroxy-4-methyl-cyclohexyl)-3-[4-methoxy-7-(tetrahydro-pyran-4-yl)-benzothiazol-2-yl]-1-methyl-urea, 3-[4-methoxy-7-(tetrahydro-pyran-4-yl)-benzothiazol-2-yl]-1-methyl-1-(tetrahydro-pyran-4-yl)-urea, 3-[4-methoxy-7-(tetrahydro-pyran-4-yl)-benzothiazol-2-yl]-1-methyl-1-(tetrahydro-furan-3-ylmethyl)-urea, (rac)-(exo)-3-[4-methoxy-7-(tetrahydro-pyran-4-yl)-benzothiazol-2-yl]-1-methyl-1-(7-oxa-bicyclo[2.2.1]hept-2-yl)-urea, (rac)-(endo)-3-[4-methoxy-7-(tetrahydro-pyran-4-yl)-benzothiazol-2-yl]-1-methyl-1-(7-oxa-bicyclo[2.2.1]hept-2-yl)-urea, 4-isopropyl-piperazine-1-carboxylic acid [4-methoxy-7-(tetrahydro-pyran-4-yl)-benzothiazol-2-yl]-amide, 1,4-dioxa-8-aza-spiro[4.5]decane-8-carboxylic acid [4-methoxy-7-(tetrahydro-pyran-4-yl)-benzothiazol-2-yl]-amide, 4-hydroxy-4-methyl-piperidine-1-carboxylic acid [4-methoxy-7-(tetrahydro-pyran-4-yl)-benzothiazol-2-yl]-amide, (2S,4S)-2-oxa-5-aza-bicyclo[2.2.1]heptane-5-carboxylic acid [4-methoxy-7-(tetrahydro-pyran-4-yl)-benzothiazol-2-yl]-amide, 2-aza-bicyclo[2.2.2]octane-2-carboxylic acid [4-methoxy-7-(tetrahydro-pyran-4-yl)-benzothiazol-2-yl]-amide, N-[4-methoxy-7-(tetrahydro-pyran-4-yl)-benzothiazol-2-yl]-2-(tetrahydro-pyran-4-yl)-acetamide, N-[4-methoxy-7-(tetrahydro-pyran-4-yl)-benzothiazol-2-yl]-2-morpholin-4-ylmethyl-isonicotinamide, 2-[(2-methoxy-ethylamino)-methyl]-N-[4-methoxy-7-(tetrahydro-pyran-4-yl)-benzothiazol-2-yl]-isonicotinamide, (trans)-2-(4-Hydroxy-cyclohexyl)-N-[4-methoxy-7-(tetrahydro-pyran-4-yl)-benzothiazol-2-yl]-acetamide, 4-Hydroxymethyl-piperidine-1-carboxylic acid [4-methoxy-7-(tetrahydro-pyran-4-yl)-benzothiazol-2-yl]-amide, (exo)-(+)-3-[4-Methoxy-7-(tetrahydro-pyran-4-yl)-benzothiazol-2-yl]-1-methyl-1-(7-oxa-bicyclo[2.2.1]hept-2-yl)-urea and (exo)-(−)-3-[4-Methoxy-7-(tetrahydro-pyran-4-yl)-benzothiazol-2-yl]-1-methyl-1-(7-oxa-bicyclo[2.2.1]hept-2-yl)-urea.

One aspect of the present compounds of formula I and their pharmaceutically acceptable salts can be prepared by methods known in the art, for example, by processes described below, which process comprises reacting a compound of formula

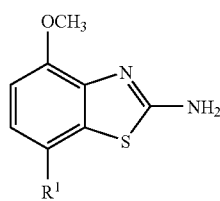

with a compound of formula

           III to produce a compound of formula

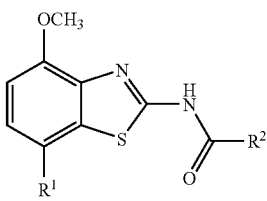           I wherein R¹ and R² are as defined above.

Another aspect of the present compounds of formula I and their pharmaceutically acceptable salts can be prepared by methods known in the art, for example, by a process described below, which process comprises reacting a compound of formula

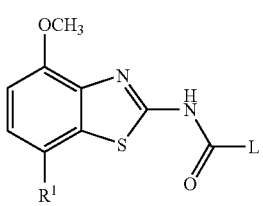           IV with a compound of formula

to produce a compound of formula

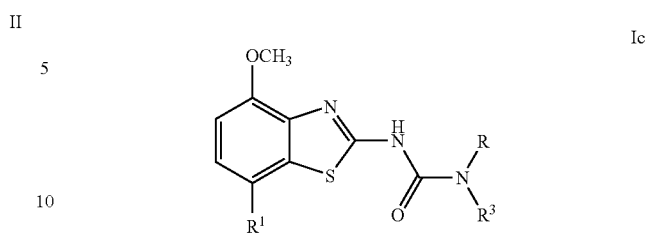

wherein R¹ and R are as defined above, L is a leaving group such as halogen, —O-phenyl or O-lower alkyl, and R³ is —(CH₂)$_n$-5- or 6 membered non aromatic heterocycle, optionally substituted by one or two substituents, selected from the group consisting of lower alkyl or —NR₂, or is cycloalkyl, optionally substituted by hydroxy or lower alkyl, or is 7-oxa-bicyclo[2.2.1]hept-2-yl; and if desired, converting the compounds obtained into pharmaceutically acceptable salts.

In Examples 1-56 and in the following schemes 1-3, the preparation of compounds of formula I is described in more detail.

The starting materials are known compounds or may be prepared according to methods known in the art.

Preparation of Compounds of Formula I

The preparation of the compound of formula Ia has been described as follows:

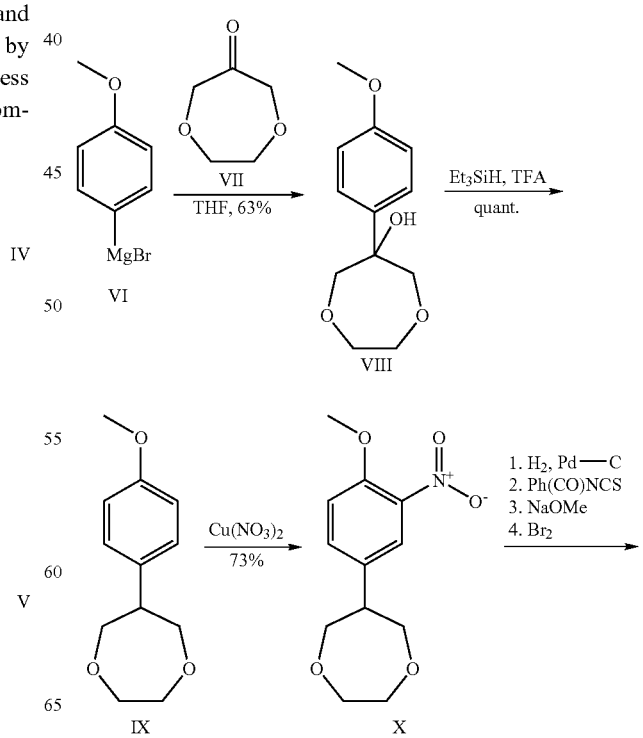

Scheme 1

-continued

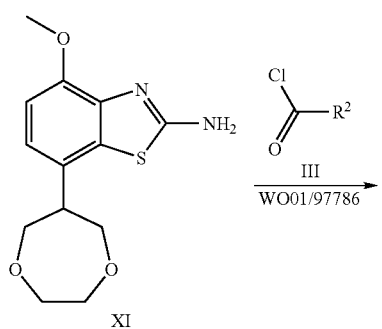

XI

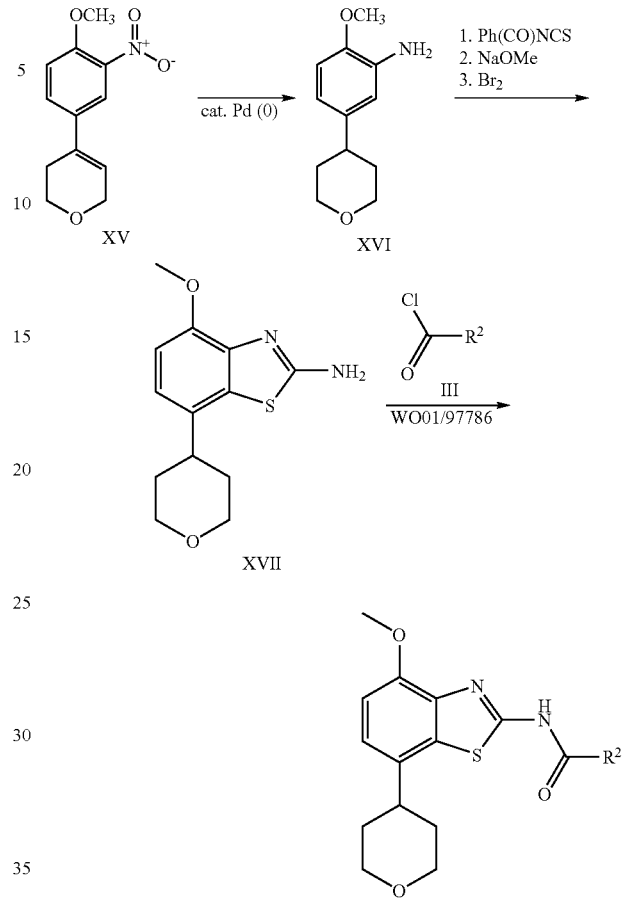

Preparation of Compounds of Formula (XI)

The intermediate 7-[1,4]dioxepan-6-yl-4-methoxy-benzothiazol-2-ylamine of formula (XI) maybe prepared starting from 6-(4-methoxy-3-nitro-phenyl)-[1,4]dioxepane (X) according to methods disclosed in WO01/97786. The preparation of compounds of formula Ia is also described in WO01/97786 and in the specific working examples. The preparation of compounds of formulas (VIII), (IX) and (X) is described in more detail in examples 36, 37 and 38.

The preparation of the intermediate of formula XVII has been described as follows:

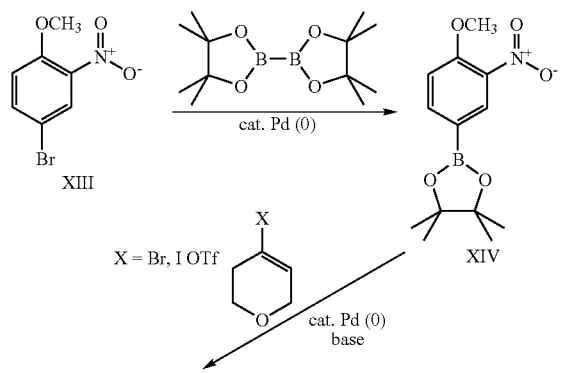

Scheme 2

Preparation of Compounds of Formula (XIV)

The aryl bromide compound of formula (XIII) is reacted with a slight excess of bis(pinacolato)diboron in an organic solvent, preferably dimethyl sulfoxide, containing a palladium catalyst, preferably dichloro(1,1'-bis(diphenylphosphino)ferrocene)palladium(II) dichloromethane adduct, and an excess of potassium acetate. The reaction is carried out at elevated temperature, preferably about 80° C., for about 2-24 hours, preferably about 2 hours. The product of formula (XIV) is isolated by conventional means, and preferably purified by means of chromatography or recrystallization.

Preparation of Compounds of Formula (XV)

One method of preparing compounds of formula (XV) is by treatment of a compound of formula (XIV) with a vinyl bromide, vinyl iodide or vinyl triflate compound in the presence of a palladium catalyst, preferably dichloro(1,1'-bis(diphenylphosphino)-ferrocene)-palladium(II) dichloromethane adduct, and an inorganic base, preferably sodium carbonate. The reaction is carried out in a mixture of solvents, preferably a mixture of ethanol, toluene and water. The reaction is carried out at elevated temperature, preferably about 80° C., for about 0.1-2 hours, preferably about 20 minutes. The product of formula (XV) is isolated by conventional means, and preferably purified by means of chromatography or recrystallization. The starting vinyl bromide, vinyl iodide or vinyl triflate compounds may be obtained commercially, for example, from Fluka, or may be prepared according to methods known in the art.

Preparation of Compounds of Formula (XVI)

Compounds of formula (XVI) may be prepared by hydrogenation of compounds of formula (XV) in the presence of a hydrogenation catalyst, preferably 10% palladium on charcoal. These reactions may be carried out in a variety of organic solvents, such as methanol, ethanol, or tetrahydrofuran, preferably methanol, at room temperature and at a pressure of one atmosphere or above, preferably at one atmosphere, for 16-72 hours, preferably about 72 hours. The product of formula (XVI) is isolated by conventional means, and preferably purified by means of chromatography or recrystallization.

Preparation of Compounds of Formula (XVII)

The intermediate 4-methoxy-7-(tetrahydro-pyran-4-yl)-benzothiazol-2-ylamine of formula (XVII) maybe prepared starting from 2-methoxy-5-(tetrahydro-pyran-4-yl)-phenylamine (XVI) according to methods disclosed in WO01/97786. The preparation of compounds of formula Ib using the intermediate of formula (XVII) is also described in WO01/97786.

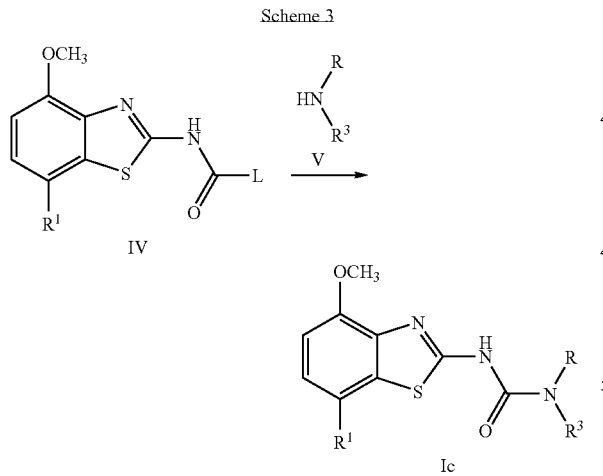

Scheme 3 wherein $R^1$ and R are as defined above, L is a leaving group such as halogen, —O-phenyl or O-lower alkyl, and $R^3$ is —$(CH_2)_n$-5- or 6 membered non aromatic heterocycle, optionally substituted by one or two substituents, selected from the group consisting of lower alkyl or —$NR_2$, or is cycloalkyl, optionally substituted by hydroxy or lower alkyl, or is 7-oxa-bicyclo[2.2.1]hept-2-yl;

In accordance with scheme 3, compounds of formula Ic may be prepared in usual manner from intermediates of formula IV (known compounds, described in WO01/97786), as described in more detail in the examples.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used.

Salts of Compounds of Formula I

The compounds of formula I may be basic, for example in cases where the residue R contains a basic group such as an aliphatic or aromatic amine moiety. In such cases the compounds of formula I may be converted to a corresponding salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic add, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are adenosine receptor ligands and possess a high affinity towards the adenosine $A_{2A}$ receptor.

The compounds were investigated in accordance with the test given hereinafter.

Human Adenosine $A_{2A}$ Receptor

The human adenosine $A_{2A}$ receptor was recombinantly expressed in chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-58261 (Dionisotti et al., 997, Br J Pharmacol 121, 353; 1 nM) binding assay was carried out in 96-well plates in the presence of 2.5 µg of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM-0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

The pKi values of compounds of the present application are in the range of 7.5 to 9.0. The preferred compounds show a pKi>8.5.

| Example No. | $Ha_2$ (pKi) |
|---|---|
| 8 | 9.0 |
| 9 | 8.7 |
| 10 | 8.9 |
| 11 | 8.6 |
| 14 | 9.0 |
| 15 | 8.7 |
| 20 | 8.6 |
| 21 | 8.6 |
| 22 | 8.6 |
| 23 | 8.7 |
| 24 | 8.5 |
| 26 | 9.0 |
| 29 | 8.8 |
| 30 | 8.9 |
| 31 | 8.9 |
| 32 | 8.7 |
| 33 | 8.8 |
| 34 | 8.7 |
| 35 | 8.8 |
| 39 | 8.8 |
| 43 | 9.4 |
| 44 | 8.6 |
| 46 | 8.6 |
| 50 | 8.6 |
| 52 | 9.0 |
| 55 | 8.9 |
| 56 | 8.5 |

The compounds of formula I and the pharmaceutically acceptable salts of the compounds of formula I can be used as medicaments, e.g., in the form of pharmaceutical preparations. The pharmaceutical preparations can be administered orally, e.g., in the form of tablets, coated tablets, dragées, hard and soft gelatin capsules, solutions, emulsions or suspensions. The administration can, however, also be effected rectally, e.g., in the form of suppositories, parenterally, e.g., in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are, however, usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

Highly preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |

-continued

Capsule Formulation

| Item | Ingredients | mg/capsule | | | |
|---|---|---|---|---|---|
| | | 5 mg | 25 mg | 100 mg | 500 mg |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following preparation and examples illustrate the invention but are not intended to limit its scope.

EXAMPLE 1

Morpholine-4-carboxylic acid (7-[1,4]dioxepan-6-yl-4-methoxy-benzothiazol-2-yl)-amide 7-[1,4]Dioxepan-6-yl-4-methoxy-benzothiazol-2-ylamine was first reacted with phenyl chloroformate as described for (4-methoxy-7-phenyl-benzothiazol-2-yl)-carbamic acid benzyl ester in WO01/97786 and then with morpholine. Usual workup, peparative reversed-phase HPLC and final dry-freezing afforded the title compound as light brown powder. MS: m/e=394(M+H$^+$).

Following the general method of example 1 the compounds of examples 2 to 7 were prepared.

EXAMPLE 2

Piperidine-1-carboxylic acid (7-[1,4]dioxepan-6-yl-4-methoxy-benzothiazol-2-yl)-amide Using 7-[1,4]dioxepan-6-yl-4-methoxy-benzothiazol-2-ylamine, phenyl chloroformate and piperidine, the title compound was prepared as light yellow powder. MS: m/e=392 (M+H$^+$).

EXAMPLE 3

1-Cyclohexyl-3-(7-[1,4]dioxepan-6-yl-4-methoxy-benzothiazol-2-yl)-1-methyl-urea

Using 7-[1,4]dioxepan-6-yl-4-methoxy-benzothiazol-2-ylamine, phenyl chloroformate and cyclohexyl-methylamine, the title compound was prepared as light off-white powder. MS: m/e=420(M+H$^+$).

EXAMPLE 4

4-Hydroxymethyl-piperidine-1-carboxylic acid (7-[1,4]dioxepan-6-yl-4-methoxy-benzothiazol-2-yl)-amide Using 7-[1,4]dioxepan-6-yl-4-methoxy-benzothiazol-2-ylamine, phenyl chloroformate and 4-hydroxymethyl-piperidine, the title compound was prepared as off-white powder. MS: m/e=422(M+H$^+$).

EXAMPLE 5

3-(7-[1,4]Dioxepan-6-yl-4-methoxy-benzothiazol-2-yl)-1-methyl-1-(1-methyl-piperidin-4-yl)-urea Using 7-[1,4]dioxepan-6-yl-4-methoxy-benzothiazol-2-ylamine, phenyl chloroformate and 1-methyl-4-(methylamino)piperidine, the title compound was prepared as light brown powder. MS: m/e=435(M+H$^+$).

EXAMPLE 6

1,4-Dioxa-8-aza-spiro[4.5]decane-8-carboxylic acid (7-[1,4]dioxepan-6-yl-4-methoxy-benzothiazol-2-yl)-amide Using 7-[1,4]dioxepan-6-yl-4-methoxy-benzothiazol-2-ylamine, phenyl chloroformate and 1,4-dioxa-8-aza-spiro[4,5]decane, the title compound was prepared as off-white powder. MS: m/e=450(M+H$^+$).

EXAMPLE 7

4-Hydroxy-piperidine-1-carboxylic acid (7-[1,4]dioxepan-6-yl-4-methoxy-benzothiazol-2-yl)-amide Using 7-[1,4]dioxepan-6-yl-4-methoxy-benzothiazol-2-ylamine, phenyl chloroformate and 4-hydroxy-piperidine, the title compound was prepared as off-white powder. MS: m/e=408(M+H$^+$).

EXAMPLE 8

5-Methyl-thiophene-2-carboxylic acid (7-[1,4]dioxepan-6-yl-4-methoxy-benzothiazol-2-yl)-amide 7-[1,4]Dioxepan-6-yl-4-methoxy-benzothiazol-2-ylamine and 5-methyl-thiophene-2-carboxylic acid were reacted as described for N-(4-methoxy-7-phenyl-benzothiazol-2-yl)-benzamide in WO01/9786. Usual workup, preparative reversed-phase HPLC and final dry-freezing afforded the title compound as white powder. MS: m/e=405 (M+H$^+$). Following the general method of example 1 the compounds of examples 9 to 16 were prepared.

EXAMPLE 9

N-(7-[1,4]Dioxepan-6-yl-4-methoxy-benzothiazol-2-yl)-4-methoxy-benzamide

Using 7-[1,4]dioxepan-6-yl-4-methoxy-benzothiazol-2-ylamine and 4-methoxy-benzoic acid, the title compound was prepared as white powder. MS: m/e=415(M+H$^+$).

EXAMPLE 10

N-(7-[1,4]Dioxepan-6-yl-4-methoxy-benzothiazol-2-yl)-4-fluoro-benzamide

Using 7-[1,4]dioxepan-6-yl-4-methoxy-benzothiazol-2-ylamine and 4-fluoro-benzoic acid, the title compound was prepared as white powder. MS: m/e=403(M+H$^+$).

EXAMPLE 11

Cyclohexanecarboxylic acid (7-[1,4]dioxepan-6-yl-4-methoxy-benzothiazol-2-yl)-amide Using 7-[1,4]dioxepan-6-yl-4-methoxy-benzothiazol-2-ylamine and cyclohexanecarboxylic acid, the title compound was prepared as white powder. MS: m/e=391 (M+H$^+$).

EXAMPLE 12

N-(7-[1,4]Dioxepan-6-yl-4-methoxy-benzothiazol-2-yl)-2-(tetrahydro-pyran-4-yl)-acetamide Using 7-[1,4]dioxepan-6-yl-4-methoxy-benzothiazol-2-ylamine and tetrahydropyran-4-yl acetic acid, the tide compound was prepared as white powder. MS: m/e=407(M+H$^+$).

EXAMPLE 13

(R)-Tetrahydro-furan-2-carboxylic acid (7-[1,4]dioxepan-6-yl-4-methoxy-benzothiazol-2-yl)-amide Using 7-[1,4]dioxepan-6-yl-4-methoxy-benzothiazol-2-ylamine and (R)-tetrahydrofuran-2-carboxylic acid, the title compound was prepared as white powder. MS: m/e=379 (M+H$^+$).

EXAMPLE 14

3-Methyl-3H-imidazole-4-carboxylic acid (7-[1,4]dioxepan-6-yl-4-methoxy-benzothiazol-2-yl)-amide Using 7-[1,4]dioxepan-6-yl-4-methoxy-benzothiazol-2-ylamine and 3-methyl-3H-imidazole-4-carboxylic acid, the title compound was prepared. MS: m/e=389(M+H$^+$).

EXAMPLE 15

N-(7-[1,4]Dioxepan-6-yl-4-methoxy-benzothiazol-2-yl)-isonicotinamide

Using 7-[1,4]dioxepan-6-yl-4-methoxy-benzothiazol-2-ylamine and isonicotinic acid, the title compound was prepared. MS: m/e=386(M+H$^+$).

EXAMPLE 16

N-(7-[1,4]Dioxepan-6-yl-4-methoxy-benzothiazol-2-yl)-2-methoxy-isonicotinamide

Using 7-[1,4]dioxepan-6-yl-4-methoxy-benzothiazol-2-ylamine and 2-methoxy-isonicotinic acid, the title compound was prepared. MS: m/e=416(M+H$^+$). Following the general method of example 1 the compounds of examples 17 to 34 were prepared.

EXAMPLE 17 trans 1-(4-Hydroxy-cyclohexyl)-3-(4-methoxy-7-[1,4]dioxepan-6-yl-benzothiazol-2-yl)-1-methyl-urea Using 7-[1,4]dioxepan-6-yl-4-methoxy-benzothiazol-2-ylamine, phenyl chloroformate and trans-4-methylamino-cyclohexanol, the title compound was prepared as off-white solid. MS: m/e=452(M+H$^+$).

EXAMPLE 18

(1S,4S)-2-Oxa-5-aza-bicyclo[2.2.1]heptane-5-carboxylic acid (7-[1,4]dioxepan-6-yl-4-methoxy-benzothiazol-2-yl)-amide Using 7-[1,4]dioxepan-6-yl-4-methoxy-benzothiazol-2-ylamine, phenyl chloroformate and (1S,4S)-2oxa-5-aza-bicyclo[2.2.1]heptane, the title compound was prepared as off-white solid. MS: m/e=422(M+H$^+$).

EXAMPLE 19

4-Methoxy-piperidine-1-carboxylic acid (7-[1,4]dioxepan-6-yl-4-methoxy-benzothiazol-2-yl)-amide Using 7-[1,4]dioxepan-6-yl-4-methoxy-benzothiazol-2-ylamine, phenyl chloroformate and 4-methoxy-piperidine, the title compound was prepared as off-white solid. MS: m/e=438(M+H$^+$).

EXAMPLE 20

3-[4-Methoxy-7-(tetrahydro-pyran-4-yl)-benzothiazol-2-yl]-1-methyl-1-(1-methyl-piperidin-4-yl)-urea Using 4-methoxy-7-(tetrahydro-pyran-4-yl)-benzothiazol-2-ylamine, phenyl chloroformate and 1-methyl-4-(methylamino)piperidine, the title compound was prepared as white crystals (56% yield). MS: m/e=419(M+H$^+$), mp 152-155° C.

EXAMPLE 21 trans-1-(4-Hydroxy-cyclohexyl)-3-[4-methoxy-7-(tetrahydro-pyran-4-yl)-benzothiazol-2-yl]-1-methyl-urea Using 4-Methoxy-7-(tetrahydro-pyran-4-yl)-benzothiazol-2-ylamine, phenyl chloroformate and (trans)-4-methylamino-cyclohexanol, the title compound was prepared as white crystals, mp 160° C., (76% yield). MS: m/e=420(M+H$^+$), mp 160° C.

EXAMPLE 22 cis-1-(4-Hydroxy-cyclohexyl)-3-[4-methoxy-7-(tetrahydro-pyran-4-yl)-benzothiazol-2-yl]-1-methyl-urea Using 4-methoxy-7-(tetrahydro-pyran-4-yl)-benzothiazol-2-ylamine, phenyl chloroformate and (cis)-4-methylamino-cyclohexanol, the title compound was prepared as white solid (70% yield). MS: m/e=420(M+H$^+$), mp 191-193° C.

EXAMPLE 23

1-(4-cis-Hydroxy-4-methyl-cyclohexyl)-3-[4-methoxy-7-(tetrahydro-pyran-4-yl)-benzothiazol-2-yl]-1-methyl-urea Using 4-methoxy-7-(tetrahydro-pyran-4-yl)-benzothiazol-2-ylamine, phenyl chloroformate and (cis)-1-methyl-4-methylamino-cyclohexanol, the title compound was prepared as white powder (64% yield). MS: m/e=434(M+H$^+$), mp 211-213° C.

EXAMPLE 24

3-[4-Methoxy-7-(tetrahydro-pyran-4-yl)-benzothiazol-2-yl]-1-methyl-1-(tetrahydro-pyran-4-yl)-urea Using 4-methoxy-7-(tetrahydro-pyran-4-yl)-benzothiazol-2-ylamine, phenyl chloroformate and methyl-(tetrahydro-pyran-4-yl)-amine, the title compound was prepared as white solid (16% yield). MS: m/e=406(M+H$^+$), mp 237-238° C.

EXAMPLE 25

3-[4-Methoxy-7-(tetrahydro-pyran-4-yl)-benzothiazol-2-yl]-1-methyl-1-(tetrahydro-furan-3-ylmethyl)-urea Using 4-methoxy-7-(tetrahydro-pyran-4-yl)-benzothiazol-2-ylamine, phenyl chloroformate and methyl-(tetrahydro-furan-3-ylmethyl)-amine, the title compound was prepared as white crystals (80% yield). MS: m/e=406(M+H$^+$), mp 185-186° C.

EXAMPLE 26

(rac)-(exo)-3-[4-Methoxy-7-(tetrahydro-pyran-4-yl)-benzothiazol-2-yl]-1-methyl-1-(7-oxa-bicyclo[2.2.1]hept-2-yl)-urea Using 4-methoxy-7-(tetrahydro-pyran-4-yl)-benzothiazol-2-ylamine, phenyl chloroformate and (exo)-methyl-(7-oxa-bicyclo[2.2.1]hept-2-yl)-amine, the title compound was prepared as white crystals (93% yield). MS: m/e=418(M+H$^+$), mp 197-200° C.

EXAMPLE 27

(rac)-(endo)-3-[4-Methoxy-7-(tetrahydro-pyran-4-yl)-benzothiazol-2-yl]-1-methyl-1-(7-oxa-bicyclo[2.2.1]hept-2-yl)-urea Using 4-methoxy-7-(tetrahydro-pyran-4-yl)-benzothiazol-2-ylamine, phenyl chloroformate and (endo)-methyl-(7-oxa-bicyclo[2.2.1]hept-2-yl)-amine, the title compound was prepared as white crystals (45% yield). MS: m/e=418(M+H$^+$), mp 214-216° C.

EXAMPLE 28

4-Isopropyl-piperazine-1-carboxylic acid [4-methoxyr7-(tetrahydro-pyran-4-yl)-benzothiazol-2-yl]-amide Using 4-methoxy-7-(tetrahydro-pyran-4-yl)-benzothiazol-2-ylamine, phenyl chloroformate and 1-isopropyl-piperazine, the title compound was prepared as light yellow crystals (36% yield). MS: m/e=419(M+H$^+$), mp 200-204° C.

EXAMPLE 29

1,4-Dioxa-8-aza-spiro[4.5]decane-8-carboxylic acid [4-methoxy-7-(tetrahydro-pyran-4-yl)-benzothiazol-2-yl]-amide Using 4-methoxy-7-(tetrahydro-pyran-4-yl)-benzothiazol-2-ylamine, phenyl chloroformate and 1,4-dioxa-8-aza-spiro[4.5]decane, the title compound was prepared as white crystals (53% yield). MS: m/e=434(M+H$^+$), mp 208-209° C.

EXAMPLE 30

4-Hydroxy-4-methyl-piperidine-1-carboxylic acid [4-methoxy-7-(tetrahydro-pyran-4-yl)-benzothiazol-2-yl]-amide Using 4-methoxy-7-(tetrahydro-pyran-4-yl)-benzothiazol-2-ylamine, phenyl chloroformate and 4-hydroxy-4-methyl-piperidine, the title compound was prepared as off-white solid (56% yield). MS: m/e=406(M+H$^+$), mp 90-95° C.

EXAMPLE 31

(1S,4S)-2-Oxa-5-aza-bicyclo[2.2.1]heptane-5-carboxylic acid [4-methoxy-7-(tetrahydro-pyran-4-yl)-benzothiazol-2-yl]-amide Using 4-methoxy-7-(tetrahydro-pyran-4-yl)-benzothiazol-2-ylamine, phenyl chloroformate and (1S,4S)-2-aza-5-oxabicyclo-[2.2.1]heptane, the title compound was prepared as white crystals (52% yield). MS: m/e=390(M+H$^+$), mp 193-197° C.

EXAMPLE 32

2-Aza-bicyclo[2.2.2]octane-2-carboxylic acid [4-methoxy-7-(tetrahydro-pyran-4-yl)-benzothiazol-2-yl]-amide Using 4-methoxy-7-(tetrahydro-pyran-4-yl)-benzothiazol-2-ylamine, phenyl chloroformate and 2-aza-bicyclo[2.2.2]octane, the title compound was prepared as off-white crystals (53% yield). MS: m/e=402(M+H$^+$), mp 237-239° C.

EXAMPLE 33

N-[4-Methoxy-7-(tetrahydro-pyran-4-yl)-benzothiazol-2-yl]-2-(tetrahydro-pyran-4-yl)-acetamide Using 4-methoxy-7-(tetrahydro-pyran-4-yl)-benzothiazol-2-ylamine and (tetrahydro-7pyran-4-yl)-acetic acid, the title compound was prepared as light yellow crystals (17% yield). MS: m/e=391(M+H$^+$), mp 218-220° C.

EXAMPLE 34

N-[4-Methoxy-7-(tetrahydro-pyran-4-yl)-benzothiazol-2-yl]-2-morpholin-4-ylmethyl-isonicotinamide 2-Chloromethyl-N-[4-methoxy-7-(tetrahydro-pyran-4-yl)-benzothiazol-2-yl]-isonicotinamide (300 mg, 0.72 mmol) and morpholine (2.1 ml, 25 mmol) are heated to 30° C. for 30 min. The mixture is then cooled to room temperature, treated with dichloromethane (15 ml) and saturated aqueous sodium carbonate (15 ml), the phases are separated and the aqueous layer extracted twice with dichloromethane. The combined organic phases were dried over sodium sulfate and concentrated in vacuo. Flash chromatography (silica, eluent chloroform/ethyl acetate, then chloroform/methanol) afforded the title compound as white solid (60% yield). MS: m/e=469(M+H$^+$), mp 199-201° C.

EXAMPLE 35

2-[(2-Methoxy-ethylamino)-methyl]-N-[4-methoxy-7-(tetrahydro-pyran-4-yl)-benzothiazol-2-yl]-isonicotinamide The title compound was prepared from 2-chloromethyl-N-[4-methoxy-7-(tetrahydro-pyran-4-yl)-benzothiazol-2-yl]-isonicotinamide and 2-methoxy-ethylamine in the same manner as described for N-[4-methoxy-7-(tetrahydro-pyran-4-yl)-benzothiazol-2-yl]-2-morpholin-4-ylmethyl-isonicotinarmide and afforded as yellow solid (60% yield). MS: m/e=457(M+H$^+$), mp 93-95° C.

2-Chloromethyl-N-[4-methoxy-7-(tetrahydro-pyran-4-yl)-benzothiazol-2-yl]-isonicotinamide was prepared from 4-methoxy-7-(tetrahydro-pyran-4-yl)-benzothiazol-2-ylamine and and 2-chloromethyl-isonicotinic acid in exact the same manner as described for 5-methyl-thiophene-2-carboxylic acid (7-[1,4]dioxepan-6-yl-4-methoxy-benzothiazol-2-yl)-amide. Light yellow solid (60% yield). MS: m/e=419(M+H$^+$).

EXAMPLE 36

1-Oxa-8-aza-spiro[4.5]decane-8-carboxylic acid (7-[1,4]dioxepan-6-yl-4-methoxy-benzothiazol-2-yl)-amide Using 7-[1,4]dioxepan-6-yl-4-methoxy-benzothiazol-2-ylamine, phenyl chloroformate and 1-oxa-8-aza-spiro[4.5]decane, the title compound was prepared as light brown powder. MS: m/e=448(M+H$^+$).

EXAMPLE 37

4-Hydroxymethyl-4-methyl-piperidine-1-carboxylic acid (7-[1,4]dioxepan-6-yl-4-methoxy-benzothiazol-2-yl)-amide Using 7-[1,4]dioxepan-6-yl-4-methoxy-benzothiazol-2-ylamine, phenyl chloroformate and 4-hydroxymethyl-4-methyl-piperidine, the title compound was prepared as light brown powder. MS: m/e=436(M+H$^+$).

EXAMPLE 38

N-(7-[1,4]Dioxepan-6-yl-4-methoxy-benzothiazol-2-yl)-4-fluoro-3-methyl-benzamide Using 7-[1,4]dioxepan-6-yl-4-methoxy-benzothiazol-2-ylamine and 4-fluoro-3-methyl-benzoic acid, the title compound was prepared in the same manner as described for 5-methyl-thiophene-2-carboxylic acid (7-[1,4]dioxepan-6-yl-4-methoxy-benzothiazol-2-yl)-amide and obtained as light brown powder. MS: m/e=417(M+H$^+$).

EXAMPLE 39

4-Chloromethyl-N-(7-[1,4]dioxepan-6-yl-4-methoxy-benzothiazol-2-yl)-benzamide

Using 7-[1,4]dioxepan-6-yl-4-methoxy-benzothiazol-2-ylamine and 4-chloromethyl-benzoic acid, the title compound was prepared in the same manner as described for 5-methyl-thiophene-2-carboxylic acid (7-[1,4]dioxepan-6-yl-4-methoxy-benzothiazol-2-yl)-amide and obtained as light brown powder. MS: m/e=434(M+H$^+$).

EXAMPLE 40

N-(7-[1,4]Dioxepan-6-yl-4-methoxy-benzothiazol-2-yl)-4-pyrrolidin-1-ylmethyl-benzamide 4-Chloromethyl-N-(7-[1,4]dioxepan-6-yl-4-methoxy-benzothiazol-2-yl)-benzamide and pyrrolidine were reacted as described for N-(4-methoxy-7-phenyl-benzothiazol-2-yl)-4-pyrrolidin-1-ylmethyl-benzamide in WO01/9786. Usual workup, preparative reversed-phase HPLC and final dry-freezing afforded the title compound as light brown powder. MS: m/e=468(M+H$^+$).

EXAMPLE 41

2-Chloromethyl-N-(7-[1,4]dioxepan-6-yl-4-methoxy-benzothiazol-2-yl)-isonicotinamide Using 7-[1,4]dioxepan-6-yl-4-methoxy-benzothiazol-2-ylamine and 2-chloromethyl-isonicotinic acid, the title compound was prepared in the same manner as described for 5-methyl-thiophene-2-carboxylic acid (7-[1,4]dioxepan-6-yl-4-methoxy-benzothiazol-2-yl)-amide and obtained as brown solid. MS: m/e=435(M+H$^+$).

EXAMPLE 42

N-(7-[1,4]Dioxepan-6-yl-4-methoxy-benzothiazol-2-yl)-4-{[(2-methoxy-ethyl)-methyl-amino]-methyl}-benzamide 4-Chloromethyl-N-(7-[1,4]dioxepan-6-yl-4-methoxy-benzothiazol-2-yl)-benzamide and N-(2-methoxyethyl)-methylamine were reacted as described for N-(4-methoxy-7-phenyl-benzothiazol-2-yl)-4-pyrrolidin-1-ylmethyl-benzamide in WO01/97786. Usual workup, preparative reversed-phase HPLC and final dry-freezing afforded the title compound as light brown powder. MS: m/e=486(M+H$^+$).

EXAMPLE 43

1-Methyl-1H-pyrazole-4-carboxylic acid (7-[1,4]dioxepan-6-yl-4-methoxy-benzothiazol-2-yl)-amide Using 7-[1,4]dioxepan-6-yl-4-methoxy-benzothiazol-2-ylamine and 1-methyl-1H-pyrazole-4-carboxylic acid, the title compound was prepared in the same manner as described for 5-methyl-thiophene-2-carboxylic acid (7-[1,4]dioxepan-6-yl-4-methoxy-benzothiazol-2-yl)-amide and obtained as white solid. MS: m/e=389(M+H$^+$).

EXAMPLE 44

N-(7-[1,4]Dioxepan-6-yl-4-methoxy-benzothiazol-2-yl)-4-[(methyl-propionyl-amino)-methyl]-benzamide Sodium hydride (4.8 mg, 60% disp. in mineral oil, 0.2 mmol) was added to N-methylpropionamide (1 ml, 11 mmol), followed by 4-chloromethyl-N-(7-[1,4]dioxepan-6-yl-4-methoxy-benzothiazol-2-yl)-benzamide (50 mg, 1.2 mmol) and the reaction mixture was heated to 55° C. for 3 hrs. After cooling, the mixture was diluted with water (5 ml) and extracted twice with ethyl acetate (5 ml). The combined organic phases were dried with magnesium sulfate, filtered and evaporated. Final purification with preparative HPLC and final dry-freezing afforded the title compound as white solid (23 mg, 42% yield). MS: m/e=484(M+H$^+$).

EXAMPLE 45

N-(7-[1,4]Dioxepan-6-yl-4-methoxy-benzothiazol-2-yl)-2-[(2-methoxy-ethyl)-methyl-amino]-isonicotinamide N-(7-[1,4]Dioxepan-6-yl-4-methoxy-benzothiazol-2-yl)-bromo-isonicotinamide and N-(2-methoxyethyl)-methylamine were reacted as described for 2-(2-methoxy-ethylamino)-N-(4-methoxy-7-morpholin-4-yl-benzothiazol-2-yl)-isonicotinamide in WO03/043636. Usual workup, preparative reversed-phase HPLC and final dry-freezing afforded the title compound as light brown solid. MS: m/e=473(M+H$^+$).

EXAMPLE 46

N-(7-[1,4]Dioxepan-6-yl-4-methoxy-benzothiazol-2-yl)-2-pyrrolidin-1-yl-isonicotinamide N-(7-[1,4]Dioxepan-6-yl-4-methoxy-benzothiazol-2-yl)-bromo-isonicotinamide and pyrrolidine were reacted as described for 2-(2-methoxy-ethylamino)-N-(4-methoxy-7-morpholin-4-yl-benzothiazol-2-yl)-isonicotinamide in WO03/043636. Usual workup, preparative reversed-phase HPLC and final dry-freezing afforded the title compound as light brown solid. MS: m/e=455(M+H$^+$).

EXAMPLE 47

N-(7-[1,4]Dioxepan-6-yl-4-methoxy-benzothiazol-2-yl)-2-pyrrolidin-1-ylmethyl-isonicotinamide 2-Chloromethyl-N-(7-[1,4]dioxepan-6-yl-4-methoxy-benzothiazol-2-yl)-isonicotinamide and N-(2-methoxy-ethyl)-methylamine were reacted as described for 2-{[(2-methoxy-ethyl)-methyl-amino]-methyl}-N-(4-methoxy-7-morpholin-4-yl-benzothiazol-2-yl)-isonicotinamide in WO03/043636. Usual workup, preparative reversed-phase HPLC and final dry-freezing afforded the tide compound as light yellow solid (48% yield). Mp 108-111° C., MS: m/e=469(M+H$^+$).

EXAMPLE 48

N-(7-[1,4]Dioxepan-6-yl-4-methoxy-benzothiazol-2-yl)-2-{[(2-methoxy-ethyl)-methyl-amino]-methyl}-isonicotinamide 2-Chloromethyl-N-(7-[1,4]dioxepan-6-yl-4-methoxy-benzothiazol-2-yl)-isonicotinamide and pyrrolidine were reacted as described for 2-{[(2-methoxy-ethyl)-methyl-amino]-methyl}-N-(4-methoxy-7-morpholin-4-yl-benzothiazol-2-yl)-isonicotinamide in WO03/043636. Usual workup, preparative reversed-phase HPLC and final dry-freezing afforded the tide compound as light brown solid (56% yield). Mp 100-107° C., MS: m/e=487(M+H$^+$).

EXAMPLE 49

2-Bromo-N-(7-[1,4]dioxepan-6-yl-4-methoxy-benzothiazol-2-yl)-isonicotinamide

Using 7-[1,4]dioxepan-6-yl-4-methoxy-benzothiazol-2-ylamine and 2-bromo-isonicotinic acid, the title compound was prepared in the same manner as described for 5-methyl-thiophene-2-carboxylic acid (7-[1,4]dioxepan-6-yl-4-methoxy-benzothiazol-2-yl)-amide and obtained as off-white powder. MS: m/e=452(M+H$^+$).

EXAMPLE 50

(trans)-2-(4-Hydroxy-cyclohexyl)-N-[4-methoxy-7-(tetrahydro-pyran-4-yl)-benzothiazol-2-yl]-acetamide Using 4-methoxy-7-(tetrahydro-pyran-4-yl)-benzothiazol-2-ylamine and (4-hydroxy-cyclohexyl)-acetic acid, the title compound was prepared in the same manner as described for N-[4-methoxy-7-(tetrahydro-pyran-4-yl)-benzothiazol-2-yl]-2-(tetrahydro-pyran-4-yl)-acetamide and obtained as white crystals (25% yield). Mp 120-145° C., MS: m/e=405(M+H$^+$).

EXAMPLE 51

(R)-Tetrahydro-furan-2-carboxylic acid [4-methoxy-7-(tetrahydro-pyran-4-yl)-benzothiazol-2-yl]-amide Using 4-methoxy-7-(tetrahydro-pyran-4-yl)-benzothiazol-2-ylamine and (R)-tetrahydro-furan-2-carboxylic acid, the title compound was prepared in the same manner as described for N-[4-methoxy-7-(tetrahydro-pyran-4-yl)-benzothiazol-2-yl]-2-(tetrahydro-pyran-4-yl)-acetamide and obtained as off-white solid (62% yield). Mp 158-161° C., MS: m/e=363(M+H$^+$).

EXAMPLE 52

4-Hydroxymethyl-piperidine-1-carboxylic acid [4-methoxy-7-(tetrahydro-pyran-4-yl)-benzothiazol-2-yl]-amide Using 4-methoxy-7-(tetrahydro-pyran-4-yl)-benzothiazol-2-ylamine, phenyl chloroformate and 4-hydroxymethyl-piperidine, the title compound was prepared as white crystals (87% yield). Mp. 202-203.5° C., MS: m/e=406(M+H$^+$).

EXAMPLE 53

1-(1-Dimethylamino-piperidin-4-yl)-3-[4-methoxy-7-(tetrahydro-pyran-4-yl)-benzothiazol-2-yl]-1-methyl-urea Using 4-methoxy-7-(tetrahydro-pyran-4-yl)-benzothiazol-2-ylamine, phenyl chloroformate and N,N,N'-Trimethyl-piperidine-1,4-diamine, the title compound was prepared as white crystals (77% yield). Mp. 167-170° C., MS: m/e=448(M+H$^+$).

EXAMPLE 54

N-[4-Methoxy-7-(tetrahydro-pyran-4-yl)-benzothiazol-2-yl]-2-(tetrahydro-furan-2-yl)-acetamide Using 4-methoxy-7-(tetrahydro-pyran-4-yl)-benzothiazol-2-ylamine and (tetrahydro-furan-2-yl)-acetic acid, the title compound was prepared in the same manner as described for N-[4-methoxy-7-(tetrahydro-pyran-4-yl)-benzothiazol-2-yl]-2-(tetrahydro-pyran-4-yl)-acetamide and obtained as white solid (50% yield). Mp 170-174° C., MS: m/e=377(M+H$^+$).

EXAMPLE 55

(exo)-(+)-3-[4-Methoxy-7-(tetrahydro-pyran-4-yl)-benzothiazol-2-yl]-1-methyl-1-(7-oxa-bicyclo[2.2.1]hept-2-yl)-urea Using 4-methoxy-7-(tetrahydro-pyran-4-yl)-benzothiazol-2-ylamine, phenyl chloroformate and (exo)-methyl-(7-oxa-bicyclo[2.2.1]hept-2-yl)-amine, the title compound was prepared as racemate. Chiral resolution on Chiralpak AD (eluent 20% EtOH in heptane) afforded the first eluting isomer as white crystals (39% yield). Mp. 185-188° C., MS: m/e=418(M+H$^+$).

EXAMPLE 56

(exo)-(−)-3-[4-Methoxy-7-(tetrahydro-pyran-4-yl]-benzothiazol-2-yl)-1-methyl-1-(7-oxa-bicyclo[2.2.1]hept-2-yl)-urea Using 4-methoxy-7-(tetrahydro-pyran-4-yl)-benzothiazol-2-ylamine, phenyl chloroformate and (exo)-methyl-(7-oxa-bicyclo[2.2.1]hept-2-yl)-amine, the title compound was prepared as racemate. Chiral resolution on Chiralpak AD (eluent 20% EtOH in heptane) afforded the second eluting isomer as white solid (29% yield). Mp. 155-190° C., MS: m/e=418(M+H$^+$).

Intermediates

EXAMPLE 57

6-(4-methoxyphenyl)-[1,4]-dioxepan-6-ol (VIII)

Magnesium (1.27 g, 0.053 mol), dried in an oven for 1 hr at 75° C., was stirred with THF (125 mL) in a 500 mL three-necked flask at reflux. A crystal of iodine was added followed by a solution of 4-methoxybromobenzene in THF (50 mL), added dropwise over 15 min. After the addition of 10 mL of the solution the reaction initiated. After complete addition of the solution, the reaction mixture was heated at reflux for 2 hrs. The resulting grey solution was cooled to 0° C. and a solution of 1,4-dioxepan-6-one (prepared as described in U.S. Pat. No. 4,410,354) (5.08 g, 0.044 mol) in THF (25 mL) was added dropwise. The reaction mixture was stirred at room temperature overnight then evaporated. The residue was acidified to pH=1 with 1N HCl and extracted with ether (2×250 mL). The ether extracts were washed with water, dried (MgSO$_4$), filtered and concentrated to give a sticky brown solid (9.45 g). This was purified by column chromatography on silica gel eluting with ethyl acetate-hexanes. The relevant fractions were concentrated to give the desired product (6.21 g, 63%).

EXAMPLE 58

6-(4-methoxyphenyl)-[1,4]-dioxepane (IX)

To a solution of 6-(4-methoxyphenyl)-[1,4]-dioxepan-6-ol (6.20 g, 0.028 mol) in CH$_2$Cl$_2$ was added triethylsilane (3.53 g, 0.031 mol) and trifluoroacetic acid (35.1 g, 0.31 mol). The reaction mixture was allowed to stir overnight. The reaction was made basic with K$_2$CO$_3$ solution until pH=10. The organic layer was dried (MgSO$_4$), filtered and evaporated to dryness to give the desired product as a red oil (5.84 g, 100%).

EXAMPLE 59

6-(4-methoxy-3-nitro-phenyl)-1,4-dioxepane (X)

A solution of 6-(4-methoxyphenyl)-1,4-dioxepane (5.84 g, 0.028 mol) and acetic anhydride (40 mL) in a 100 mL three-necked flask was heated to 65° C. The heat was removed and the copper (II) nitrate (7.7 g, 0.033 mol) was added portionwise over 2 hrs while the temperature was maintained between 60-70° C. (caution: exothermic). When the addition was complete the blue suspension was stirred at 65° C. for an additional 1.5 hr. Water (400 mL) was added and the reaction mixture was stirred for 1 hour then solid K$_2$CO$_3$ was added until pH=10. The mixture was extracted with ethyl acetate (3×150 mL). The combined organics were dried (MgSO$_4$), filtered and evaporated to give a red oil (7.37 g). The crude material was purified by column chromatography eluting with 20%-30% EtOAc-hexanes. The relevant fractions were combined and concentrated to give the desired product as an orange oil (5.80 g, 83%). MS: m/e=254(M+H$^+$).

EXAMPLE 60

7-[1,4]Dioxepan-6-yl-4-methoxy-benzothiazol-2-ylamine (XI)

The title compound was prepared from 6-(4-methoxy-3-nitro-phenyl)-1,4-dioxepane in exact the same manner as described in WO01/97786 for 4-methoxy-7-phenoxy-benzothiazol-2-yl-amine in 57% yield (3.7 g). MS: m/e=281 (M+H$^+$).

EXAMPLE 61

4-Methoxy-7-(tetrahydro-pyran-4-yl)-benzothiazol-2-yl-amine (XVII)

a) 2-(4-Methoxy-3-nitro-phenyl)-4,4,5,5-tetramethyl-1,3,21 dioxaborolane

To a stirred solution of 1.30 g (5.60 mmol) 4-bromo-2-nitroanisole in 25 ml DMSO were added 1.57 g (6.16 mmol) bis(pinacolato)diboron, 123 mg (0.17 mmol) dichloro(1,1'-bis(diphenylphosphino)ferrocene)palladium(II) dichloromethane adduct and 1.65 g (16.8 mmol) potassium acetate. The mixture was heated at 80° C. for 2 h and then cooled to room temperature, poured onto water, and extracted three times with ethyl acetate. The combined organic phases were dried over sodium sulfate and concentrated in vacuo. Flash chromatography (1/2 ethyl acetate/hexane then ethyl acetate) afforded 1.39 g 2-(4-methoxy-3-nitro-phenyl)-4,4,5,5-tetramethyl-[1,3,2]dioxaborolane as an off-white solid. ES-MS m/e (%): 280 (M+H$^+$, 100).

b) 4-(4-Methoxy-3-nitro-phenyl)-3,6-dihydro-2H-pyran

To a stirred solution of 4.36 g (15.6 mmol) 2-(4-methoxy-3-nitro-phenyl)-4,4,5,5-tetramethyl-[1,3,2]dioxaborolane and 3.30 g (14.2 mmol) trifluoromethanesulfonic acid 3,6-dihydro-2H-pyran-4-yl ester in 33 ml ethanol and 82 ml toluene was added 580 mg (0.71 mmol) dichloro(1,1'-bis(diphenylphosphino)ferrocene)palladium(II) dichloromethane adduct. The mixture was heated at 80° C. and 16.5 ml (33.0 mmol) 2 M aqueous sodium carbonate solution was added dropwise. The reaction mixture was stirred for 20 minutes at 80° C. and then cooled to room temperature, poured onto water, and extracted three times with ethyl acetate. The combined organic phases were dried over sodium sulfate and concentrated in vacuo. Flash chromatography (1/4 ethyl acetate/hexane) afforded 2.00 g (60%) 4-(4-methoxy-3-nitro-phenyl)-3,6-dihydro-2H-pyran as a light yellow solid. ES-MS m/e (%): 253 (M+NH$_4^+$, 100), 236 (M+H$^+$, 24).

c) 2-Methoxy-5-(tetrahydro-pyran-4-yl)-phenylamine

To a stirred solution of 3.30 g (14.0 mmol) 4-(4-methoxy-3-nitro-phenyl)-3,6-dihydro-2H-pyran in 70 ml methanol and 70 ml dichloromethane was added a spatula end of 10% palladium on charcoal and the mixture was then stirred for 20 minutes at room temperature under an atmosphere of hydrogen. The mixture was then filtered, washing with dichloromethane, and the filtrate concentrated in vacuo to afford 2.75 g (95%) 2-methoxy-5-(tetrahydro-pyran-4-yl)-phenylamine as an off-white crystalline solid. ES-MS m/e (%): 208 (M+H$^+$, 100).

d) 1-Benzoyl-3-[2-methoxy-5-(tetrahydro-pyran-4-yl)-phenyl]-thiourea

To a stirred solution of 1.11 g (14.6 mmol) ammonium rhodanide in 60 ml acetone was added dropwise 1.54 ml (13.3 mmol) benzoyl chloride and the mixture heated at reflux for 10 minutes. A solution of 2.75 g (13.3 mmol) 2-methoxy-5-(tetrahydro-pyran-4-yl)-phenylamine in 30 ml acetone was then added dropwise and the reaction mixture heated at reflux for a further 10 minutes. The mixture was then cooled to room temperature, poured onto sodium bicarbonate solution, and extracted three times with dichloromethane. The combined organic phases were dried over sodium sulfate and concentrated in vacuo. Flash chromatography (1/1 ethyl acetate/hexane) followed by trituration in ether afforded 3.25 g (66%) 1-benzoyl-3-[2-methoxy-5-(tetrahydro-pyran-4-yl)-phenyl]-thiourea as a white solid. ES-MS m/e (%): 371 (M+H$^+$, 100).

e) [2-Methoxy-5-(tetrahydro-pyran-4-yl)-phenyl]-thiourea

To a stirred solution of 3.25 g (8.77 mmol) 1-benzoyl-3-[2-methoxy-5-(tetrahydro-pyran-4-yl)-phenyl]-thiourea in 45 ml methanol was added dropwise 0.25 ml (1.32 mmol) 5.3 M sodium methylate solution and stirring continued for 1 h at room temperature. The mixture was then poured onto water and extracted three times with ethyl acetate. The combined organic phases were dried over sodium sulfate and concentrated in vacuo. Flash chromatography (ethyl acetate) afforded 1.90 g (81%) [2-methoxy-5-(tetrahydro-pyran-4-yl)-phenyl]-thiourea as a white foam. ES-MS m/e (%): 267 (M+H$^+$, 100).

f) 4-Methoxy-7-(tetrahydro-pyran-4-yl)-benzothiazol-2-ylamine

To a stirred solution of 1.90 g (7.13 mmol) [2-methoxy-5-(tetrahydro-pyran-4-yl)-phenyl]-thiourea in 20 ml acetic acid heated to 80° C. was added dropwise 1.45 ml (8.27 mmol) hydrobromic acid (5.7 M solution in acetic acid) and stirring continued for 30 min at 80° C. 0.56 ml (7.85 mmol) DMSO was then added dropwise and the reaction mixture stirred for a further 30 min at 80° C. The mixture was then cooled to room temperature, poured slowly onto sodium bicarbonate solution, and ethyl acetate added. The mixture was stirred for 10 minutes at room temperature and the resulting crystals collected by filtration, washing with ethyl acetate. The mother liquor phases were separated and the organic phase concentrated in vacuo to 5 ml. The resulting second crop of crystals was collected by filtration and combined with the first crop to afford 920 mg (49%) 4-methoxy-7-(tetrahydro-pyran-4-yl)-benzothiazol-2-ylamine as a white solid. ES-MS m/e (%): 265 (M+H$^+$, 100).

The invention claimed is:

1. A compound of formula I

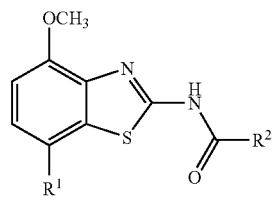

wherein

R$^1$ is selected from 1,4-dioxepanyl and tetrahydropyran-4-yl;

R$^2$ is selected from
—N(R)—(CH$_2$)$_n$-5 membered non aromatic heterocycle,
—N(R)—(CH$_2$)$_n$-5 membered non aromatic heterocycle substituted by one or two substituents selected from lower alkyl, (CH$_2$)$_n$—OH and —NR$_2$,
—N(R)—(CH$_2$)$_n$-6 membered non aromatic heterocycle,
—N(R)—(CH$_2$)$_n$-6 membered non aromatic heterocycle substituted by one or two substituents selected from lower alkyl, (CH$_2$)$_n$—OH and —NR$_2$,
—(CH$_2$)$_n$-5 membered non aromatic heterocycle,
—(CH$_2$)$_n$-5 membered non aromatic heterocycle substituted by one or two substituents selected from —(CH$_2$)$_n$—OH, lower alkyl and lower alkoxy,
—(CH$_2$)$_n$-6 membered non aromatic heterocycle,
—(CH$_2$)$_n$-6 membered non aromatic heterocycle substituted by one or two substituents selected from —(CH$_2$)$_n$—OH, lower alkyl and lower alkoxy
—(CH$_2$)$_n$-5 membered aromatic heterocycle,
—(CH$_2$)$_n$-5 membered aromatic heterocycle substituted by one or two substituents selected from the group consisting of lower alkyl, lower alkoxy, halogen, halogen-lower alkyl, —CH$_2$N(R)(CH$_2$)$_2$OCH$_3$, —N(R)(CH$_2$)$_2$OCH$_3$, —CH$_2$-morpholinyl and —CH$_2$-pyrrolidinyl,
—(CH$_2$)$_n$-6 membered aromatic heterocycle,
—(CH$_2$)$_n$-6 membered aromatic heterocycle substituted by one or two substituents selected from the group consisting of lower alkyl, lower alkoxy, halogen, halogen-lower alkyl, —CH$_2$N(R)(CH$_2$)$_2$OCH$_3$, —N(R)(CH$_2$)$_2$OCH$_3$, —CH$_2$-morpholinyl and —(CH$_2$)$_n$-pyrrolidinyl,
(CH$_2$)$_n$-cycloalkyl,
(CH$_2$)$_n$-cycloalkyl substituted by hydroxy,
—N(R)—(CH$_2$)$_n$-cycloalkyl,
—N(R)—(CH$_2$)$_n$-cycloalkyl substituted by a substituent selected from hydroxy and lower alkyl, —N(R)—(CH$_2$)$_n$-phenyl,
phenyl,
phenyl substituted by one or two substituents selected from the group consisting of lower alkoxy, halogen, halogen-lower alkyl, lower alkyl, —CH$_2$-pyrrolidin-1-yl, —CH$_2$-morpholinyl, —CH$_2$N(R)(CH$_2$)$_2$OCH$_3$ and —CH$_2$—N(R)C(O)-lower alkyl,
1,4-dioxa-8-aza-spiro[4,5]decane,
2-oxa-5-aza-bicyclo[2.2.1]heptane,
1-oxa-8-aza-spiro[4,5]decane,
—N(R)—(CH$_2$)$_n$-7-oxa-bicyclo[2.2.1]hept-2-yl, and
2-aza-bicyclo[2.2.2]decane;
R is selected from hydrogen or lower alkyl;
n is 0 or 1;
or a pharmaceutically acceptable salt thereof.

2. A compound of formula I

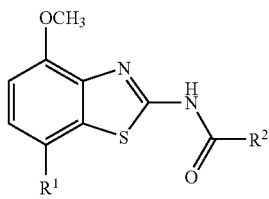

wherein
R$^1$ is 1,4-dioxepanyl;
R$^2$ is selected from
—N(R)—(CH$_2$)$_n$-5 membered non aromatic heterocycle,
—N(R)—(CH$_2$)$_n$-5 membered non aromatic heterocycle substituted by one or two substituents selected from lower alkyl, (CH$_2$)$_n$—OH and —NR$_2$,
—N(R)—(CH$_2$)$_n$-6 membered non aromatic heterocycle,
—N(R)—(CH$_2$)$_n$-6 membered non aromatic heterocycle substituted by one or two substituents selected from lower alkyl, (CH$_2$)$_n$—OH and —NR$_2$,
—(CH$_2$)$_n$-5 membered non aromatic heterocycle,
—(CH$_2$)$_n$-5 membered non aromatic heterocycle substituted by one or two substituents selected from —(CH$_2$)$_n$—OH, lower alkyl and lower alkoxy,
—(CH$_2$)$_n$-6 membered non aromatic heterocycle,
—(CH$_2$)$_n$-6 membered non aromatic heterocycle substituted by one or two substituents selected from —(CH$_2$)$_n$—OH, lower alkyl and lower alkoxy
—(CH$_2$)$_n$-5 membered aromatic heterocycle,
—(CH$_2$)$_n$-5 membered aromatic heterocycle substituted by one or two substituents selected from the group consisting of lower alkyl, lower alkoxy, halogen, halogen-lower alkyl, —CH$_2$N(R)(CH$_2$)$_2$OCH$_3$, —N(R)(CH$_2$)$_2$OCH$_3$, —CH$_2$-morpholinyl and —CH$_2$-pyrrolidinyl,
—(CH$_2$)$_n$-6 membered aromatic heterocycle,
—(CH$_2$)$_n$-6 membered aromatic heterocycle substituted by one or two substituents selected from the group consisting of lower alkyl, lower alkoxy, halogen, halogen-lower alkyl, —CH$_2$N(R)(CH$_2$)$_2$OCH$_3$, —N(R)(CH$_2$)$_2$OCH$_3$, —CH$_2$-morpholinyl and —(CH$_2$)$_n$-pyrrolidinyl,
(CH$_2$)$_n$-cycloalkyl,
(CH$_2$)$_n$-cycloalkyl substituted by hydroxy,
—N(R)—(CH$_2$)$_n$-cycloalkyl,
—N(R)—(CH$_2$)$_n$-cycloalkyl substituted by a substituent selected from hydroxy and lower alkyl,
—N(R)—(CH$_2$)$_n$-phenyl,
phenyl,
phenyl substituted by one or two substituents selected from the group consisting of lower alkoxy, halogen, halogen-lower alkyl, lower alkyl, —CH$_2$-pyrrolidin-1-yl, —CH$_2$-morpholinyl, —CH$_2$N(R)(CH$_2$)$_2$OCH$_3$ and —CH$_2$—N(R)C(O)-lower alkyl,
1,4-dioxa-8-aza-spiro[4,5]decane,
2-oxa-5-aza-bicyclo[2.2.1]heptane,
1-oxa-8-aza-spiro[4,5]decane,
—N(R) —(CH$_2$)$_n$-7-oxa-bicyclo[2.2.1]hept-2-yl, and
2-aza-bicyclo[2.2.2]decane;
R is selected from hydrogen or lower alkyl; and
n is 0 or 1;
or a pharmaceutically acceptable salt thereof.

3. A compound of formula I

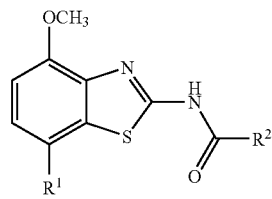

wherein
R$^1$ is 1,4-dioxepanyl;
R$^2$ is selected from
—N(R)—(CH$_2$)$_n$-6 membered non aromatic heterocycle,
—N(R)—(CH$_2$)$_n$-6 membered non aromatic heterocycle substituted by one or two substituents selected from lower alkyl and (CH$_2$)$_n$—OH,
—(CH$_2$)$_n$-5 membered non aromatic heterocycle,
—(CH$_2$)$_n$-6 membered non aromatic heterocycle,
—(CH$_2$)$_n$-6 membered non aromatic heterocycle substituted by —(CH$_2$)$_n$—OH
—(CH$_2$)$_n$-5 membered aromatic heterocycle substituted by one or two substituents selected from the group consisting of lower alkyl,
—(CH$_2$)$_n$-6 membered aromatic heterocycle,
—(CH$_2$)$_n$-6 membered aromatic heterocycle substituted by one or two substituents selected from the group consisting of lower alkoxy, halogen, —CH$_2$N(R)(CH$_2$)$_2$OCH$_3$, and —(CH$_2$)$_n$-pyrrolidinyl,
(CH$_2$)$_n$-cycloalkyl,
—N(R)-cycloalkyl substituted by hydroxy,
phenyl substituted by one or two substituents selected from the group consisting of halogen, lower alkyl, —CH$_2$-pyrrolidin-1-yl, —CH$_2$N(R)(CH$_2$)$_2$OCH$_3$ and —CH$_2$—N(R)C(O)-lower alkyl,
1,4-dioxa-8-aza-spiro[4,5]decane,
2-oxa-5-aza-bicyclo[2.2.1]heptane, and
1-oxa-8-aza-spiro[4,5]decane;
R is selected from hydrogen or lower alkyl; and
n is 0 or 1;
or a pharmaceutically acceptable salt thereof.

4. A compound of the formula I

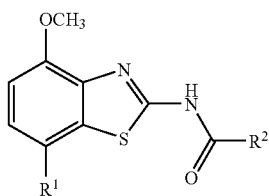

wherein
$R^1$ is tetrahydropyran-4-yl;
$R^2$ is selected from
- —N(R)—$(CH_2)_n$-5 membered non aromatic heterocycle,
- —N(R)—$(CH_2)_n$-5 membered non aromatic heterocycle substituted by one or two substituents selected from lower alkyl, $(CH_2)_n$—OH and —$NR_2$,
- —N(R)—$(CH_2)_n$-6 membered non aromatic heterocycle,
- —N(R)—$(CH_2)_n$-6 membered non aromatic heterocycle substituted by one or two substituents selected from lower alkyl, $(CH_2)_n$—OH and —$NR_2$,
- —$(CH_2)_n$-5 membered non aromatic heterocycle,
- —$(CH_2)_n$-5 membered non aromatic heterocycle substituted by one or two substituents selected from —$(CH_2)_n$—OH, lower alkyl and lower alkoxy,
- —$(CH_2)_n$-6 membered non aromatic heterocycle,
- —$(CH_2)_n$-6 membered non aromatic heterocycle substituted by one or two substituents selected from —$(CH_2)_n$—OH, lower alkyl and lower alkoxy
- —$(CH_2)_n$-5 membered aromatic heterocycle,
- —$(CH_2)_n$-5 membered aromatic heterocycle substituted by one or two substituents selected from the group consisting of lower alkyl, lower alkoxy, halogen, halogen-lower alkyl, —$CH_2N(R)(CH_2)_2OCH_3$, —$N(R)(CH_2)_2OCH_3$, —$CH_2$-morpholinyl and —$CH_2$-pyrrolidinyl,
- —$(CH_2)_n$-6 membered aromatic heterocycle,
- —$(CH_2)_n$-6 membered aromatic heterocycle substituted by one or two substituents selected from the group consisting of lower alkyl, lower alkoxy, halogen, halogen-lower alkyl, —$CH_2N(R)(CH_2)_2OCH_3$, —$N(R)(CH_2)_2OCH_3$, —$CH_2$-morpholinyl and —$(CH_2)_n$-pyrrolidinyl,
- $(CH_2)_n$-cycloalkyl,
- $(CH_2)_n$-cycloalkyl substituted by hydroxy,
- —N(R)—$(CH_2)_n$-cycloalkyl,
- —N(R)—$(CH_2)_n$-cycloalkyl substituted by a substituent selected from hydroxy and lower alkyl,
- —N(R)—$(CH_2)_n$-phenyl,
- phenyl,
- phenyl substituted by one or two substituents selected from the group consisting of lower alkoxy, halogen, halogen-lower alkyl, lower alkyl, —$CH_2$-pyrrolidin-1-yl, —$CH_2$-morpholinyl, —$CH_2N(R)(CH_2)_2OCH_3$ and—$CH_2$—N(R)C(O)-lower alkyl,
- 1,4-dioxa-8-aza-spiro[4,5]decane,
- 2-oxa-5-aza-bicyclo[2.2.1]heptane,
- 1-oxa-8-aza-spiro[4,5]decane,
- —N(R)—$(CH_2)_n$-7-oxa-bicyclo[2.2.1]hept-2-yl, and
- 2-aza-bicyclo[2.2.2]decane;

R is selected from hydrogen or lower alkyl; and
n is 0 or 1;
or a pharmaceutically acceptable salt thereof.

5. A compound of formula I

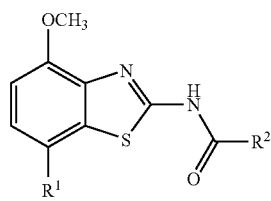

wherein
$R^1$ is tetrahydropyran-4-yl;
$R^2$ is selected from
- —N(R)—$(CH_2)_n$-5 membered non aromatic heterocycle,
- —N(R)—$(CH_2)_n$-6 membered non aromatic heterocycle,
- —N(R)—$(CH_2)_n$-6 membered non aromatic heterocycle substituted by one or two substituents selected from lower alkyl and —$NR_2$,
- —$(CH_2)_n$-5 membered non aromatic heterocycle,
- —$(CH_2)_n$-6 membered non aromatic heterocycle,
- —$(CH_2)_n$-6 membered non aromatic heterocycle substituted by one or two substituents selected from —$(CH_2)_n$—OH and lower alkyl,
- —$(CH_2)_n$-6 membered aromatic heterocycle substituted by one or two substituents selected from —$CH_2N(R)(CH_2)_2OCH_3$ and —$CH_2$-morpholinyl,
- $(CH_2)_n$-cycloalkyl substituted by hydroxy,
- —N(R)—$(CH_2)_n$-cycloalkyl substituted by a group selected from hydroxy and lower alkyl,
- —N(R)—$(CH_2)_n$-phenyl,
- 1,4-dioxa-8-aza-spiro[4,5]decane,
- 2-oxa-5-aza-bicyclo[2.2.1]heptane,
- —N(R)—$(CH_2)_n$-7-oxa-bicyclo[2.2.1]hept-2-yl, and
- 2-aza-bicyclo[2.2.2]decane;

R is selected from hydrogen or lower alkyl; and
n is 0 or 1;
or a pharmaceutically acceptable salt thereof.

6. The compound of formula I in accordance with claim 3, which is selected from
- morpholine-4-carboxylic acid (7-[1,4]dioxepan-6-yl-4-methoxy-benzothiazol-2-yl)-amide,
- piperidine-1-carboxylic acid (7-[1,4]dioxepan-6-yl-4-methoxy-benzothiazol-2-yl)-amide,
- 1-cyclohexyl-3-(7-[1,4]dioxepan-6-yl-4-methoxy-benzothiazol-2-yl)-1-methyl-urea,
- 4-hydroxymethyl-piperidine-1-carboxylic acid (7-[1,4]dioxepan-6-yl-4-methoxy-benzothiazol-2-yl)-amide,
- 3-(7-[1,4]dioxepan-6-yl-4-methoxy-benzothiazol-2-yl)-1-methyl-1-(1-methyl-piperidin-4-yl)-urea,
- 1,4-dioxa-8-aza-spiro[4,5]decane-8-carboxylic acid (7-[1,4]dioxepan-6-yl-4-methoxy-benzothiazol-2-yl)-amide,
- 4-hydroxy-piperidine-1-carboxylic acid (7-[1,4]dioxepan-6-yl-4-methoxy-benzothiazol-2-yl) -amide,
- 5-methyl-thiophene-2-carboxylic acid (7-[1,4]dioxepan-6-yl-4-methoxy-benzothiazol-2-yl)-amide,
- N-(7-[1,4]dioxepan-6-yl-4-methoxy-benzothiazol-2-yl)-4-methoxy-benzamide, and
- N-(7-[1,4]dioxepan-6-yl-4-methoxy-benzothiazol-2-yl)-4-fluoro-benzamide.

7. The compound of formula I in accordance with claim 3, which is selected from cyclohexanecarboxylic acid (7-[1,4]dioxepan-6-yl-4-methoxy-benzothiazol-2-yl)-amide,
N-(7-[1,4]dioxepan-6-yl-4-methoxy-benzothiazol-2-yl)-2-(tetrahydro-pyran-4-yl)-acetamide,
(R)-tetrahydro-furan-2-carboxylic acid (7-[1,4]dioxepan-6-yl-4-methoxy-benzothiazol-2-yl)-amide,
3-methyl-3H-imidazole-4-carboxylic acid (7-[1,4]dioxepan-6-yl-4-methoxy-benzothiazol-2-yl)-amide,
N-(7-[1,4]dioxepan-6-yl-4-methoxy-benzothiazol-2-yl)-isonicotinamide and
N-(7-[1,4]dioxepan-6-yl-4-methoxy-benzothiazol-2-yl)-2-methoxy-isonicotinamide.

8. The compound of formula I in accordance with claim 3, which is selected from
trans 1-(4-hydroxy-cyclohexyl)-3-(4-methoxy-7-[1,4]dioxepan-6-yl-benzothiazol-2-yl)-1-methyl-urea,
(1S,4S)-2oxa-5-aza-bicyclo[2.2.1]heptane-5-carboxylic acid (7-[1,4]dioxepan-6-yl-4-methoxy-benzothiazol-2-yl)-amide,
4-methoxy-piperidine-1-carboxylic acid (7-[1,4]dioxepan-6-yl-4-methoxy-benzothiazol-2-yl)-amide,
4-chloromethyl-N-(7-[1,4]dioxepan-6-yl-4-methoxy-benzothiazol-2-yl)-benzamide, 1-methyl-1H-pyrazole-4-carboxylic acid (7-[1,4]dioxepan-6-yl-4-methoxy-benzothiazol-2-yl)-amide,
N-(7-[1,4]dioxepan-6-yl-4-methoxy-benzothiazol-2-yl)-4-[(methyl-propionyl-amino)-methyl]-benzamide and
N-(7-[1,4]dioxepan-6-yl-4-methoxy-benzothiazol-2-yl)-2-pyrrolidin-1-yl-isonicotinamide.

9. The compound of formula I in accordance with claim 5, which is selected from
3-[4-methoxy-7-(tetrahydro-pyran-4-yl)-benzothiazol-2-yl]-1-methyl-1-(1-methyl-piperidin-4-yl)-urea,
trans-1-(4-hydroxy-cyclohexyl)-3-[4-methoxy-7-(tetrahydro-pyran-4-yl)-benzothiazol-2-yl]-1-methyl-urea,
cis-1-(4-hydroxy-cyclohexyl)-3-[4-methoxy-7-(tetrahydro-pyran-4-yl)-benzothiazol-2-yl]-1-methyl-urea,
1-(4-cis-hydroxy-4-methyl-cyclohexyl)-3-[4-methoxy-7-(tetrahydro-pyran-4-yl)-benzothiazol-2-yl]-1-methyl-urea,
3-[4-methoxy-7-(tetrahydro-pyran-4-yl)-benzothiazol-2-yl]-1-methyl-1-(tetrahydro-pyran-4-yl)-urea,
3-[4-methoxy-7-(tetrahydro-pyran-4-yl)-benzothiazol-2-yl]-1-methyl-1-(tetrahydro-furan-3-ylmethyl)-urea,
(rac)-(exo)-3-[4-methoxy-7-(tetrahydro-pyran-4-yl)-benzothiazol-2-yl]-1-methyl-1-(7-oxa-bicyclo[2.2.1]hept-2-yl)-urea,
(rac)-(endo)-3-[4-methoxy-7-(tetrahydro-pyran-4-yl)-benzothiazol-2-yl]-1-methyl-1-(7-oxa-bicyclo[2.2.1]hept-2-yl)-urea,
4-isopropyl-piperazine-1-carboxylic acid [4-methoxy-7-(tetrahydro-pyran-4-yl)-benzothiazol-2-yl]-amide and
1,4-dioxa-8-aza-spiro[4.5]decane-8-carboxylic acid [4-methoxy-7-(tetrahydro-pyran-4-yl)-benzothiazol-2-yl]-amide.

10. The compound of formula I in accordance with claim 5, which is selected from
4-hydroxy-4-methyl-piperidine-1-carboxylic acid [4-methoxy-7-(tetrahydro-pyran-4-yl)-benzothiazol-2-yl]-amide,
(1S,4S)-2-oxa-5-aza-bicyclo[2.2.1]heptane-5-carboxylic acid [4-methoxy-7-(tetrahydro-pyran-4-yl)-benzothiazol-2-yl]-amide,
2-aza-bicyclo[2.2.2]octane-2-carboxylic acid [4-methoxy-7-(tetrahydro-pyran-4-yl)-benzothiazol-2-yl]-amide,
N-[4-methoxy-7-(tetrahydro-pyran-4-yl)-benzothiazol-2-yl]-2-(tetrahydro-pyran-4-yl)-acetamide,
N-[4-methoxy-7-(tetrahydro-pyran-4-yl)-benzothiazol-2-yl]-2-morpholin-4-ylmethyl-isonicotinamide,
2-[(2-methoxy-ethylamino)-methyl]-N-[4-methoxy-7-(tetrahydro-pyran-4-yl)-benzothiazol-2-yl]-isonicotinamide,
(trans)-2-(4-Hydroxy-cyclohexyl)-N-[4-methoxy-7-(tetrahydro-pyran-4-yl)-benzothiazol-2-yl]-acetamide,
4-Hydroxymethyl-piperidine-1-carboxylic acid [4-methoxy-7-(tetrahydro-pyran-4-yl)-benzothiazol-2-yl]-amide,
(exo)-(+)-3-[4-Methoxy-7-(tetrahydro-pyran-4-yl)-benzothiazol-2-yl]-1-methyl-1-(7-oxa-bicyclo[2.2.1]hept-2-yl)-urea and
(exo)-(−)-3-[4-Methoxy-7-(tetrahydro-pyran-4-yl)-benzothiazol-2-yl]-1-methyl-1-(7-oxa-bicyclo[2 .2.1]hept-2-yl)-urea.

11. A process for preparing a compound of formula I which comprises reacting a compound of formula

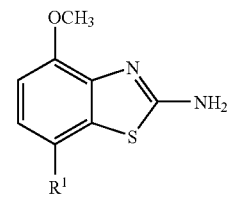

II with a compound of formula

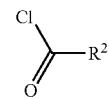

III to produce a compound of formula

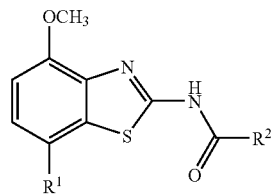

I wherein
$R^1$ is selected from 1,4-dioxepanyl and tetrahydropyran-4-yl;
$R^2$ is selected from
—N(R)—$(CH_2)_n$-5 membered non aromatic heterocycle,
—N(R)—$(CH_2)_n$-5 membered non aromatic heterocycle substituted by one or two substituents selected from lower alkyl, $(CH_2)_n$—OH and —$NR_2$,
—N(R)—$(CH_2)_n$-6 membered non aromatic heterocycle,
—N(R)—$(CH_2)_n$-6 membered non aromatic heterocycle substituted by one or two substituents selected from lower alkyl, $(CH_2)_n$—OH and —$NR_2$, —(CH$_2$)$_n$-5 membered non aromatic heterocycle,
—(CH$_2$)$_n$-5 membered non aromatic heterocycle substituted by one or two substituents selected from —(CH$_2$)$_n$—OH, lower alkyl and lower alkoxy,
—(CH$_2$)$_n$-6 membered non aromatic heterocycle,
—(CH$_2$)$_n$-6 membered non aromatic heterocycle substituted by one or two substituents selected from —(CH$_2$)$_n$—OH, lower alkyl and lower alkoxy
—(CH$_2$)$_n$-5 membered aromatic heterocycle,
—(CH$_2$)$_n$-5 membered aromatic heterocycle substituted by one or two substituents selected from the group consisting of lower alkyl, lower alkoxy, halogen, halogen-lower alkyl, —CH$_2$N(R)(CH$_2$)$_2$OCH$_3$, —N(R)(CH$_2$)$_2$OCH$_3$, —CH$_2$-morpholinyl and —CH$_2$-pyrrolidinyl,
—(CH$_2$)$_n$-6 membered aromatic heterocycle,
—(CH$_2$)$_n$-6 membered aromatic heterocycle substituted by one or two substituents selected from the group consisting of lower alkyl, lower alkoxy, halogen, halogen-lower alkyl, —CH$_2$N(R)(CH$_2$)$_2$OCH$_3$, —N(R)(CH$_2$)$_2$OCH$_3$, —CH$_2$-morpholinyl and —(CH$_2$)$_n$-pyrrolidinyl,
(CH$_2$)$_n$-cycloalkyl,
(CH$_2$)$_n$-cycloalkyl substituted by hydroxy,
—N(R)—(CH$_2$)$_n$-cycloalkyl,
—N(R)—(CH$_2$)$_n$-cycloalkyl substituted by a group selected from hydroxy and lower alkyl,
—N(R)—(CH$_2$)$_n$-phenyl,
phenyl,
phenyl substituted by one or two substituents selected from the group consisting of lower alkoxy, halogen, halogen-lower alkyl, lower alkyl, —CH$_2$-pyrrolidin-1-yl, —CH$_2$-morpholinyl, —CH$_2$N(R)(CH$_2$)$_2$OCH$_3$ and —CH$_2$—N(R)C(O)-lower alkyl,
1,4-dioxa-8-aza-spiro[4,5]decane,
2-oxa-5-aza-bicyclo[2.2.1]heptane,
1-oxa-8-aza-spiro[4,5]decane,
—N(R)—(CH$_2$)$_n$-7-oxa-bicyclo[2.2.1]hept-2-yl, and
2-aza-bicyclo[2.2.2]decane;
R is selected from hydrogen or lower alkyl; and
n is 0 or 1.

12. A process for preparing a compound of formula I which comprises reacting a compound of formula

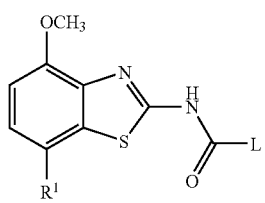

IV with a compound of formula

V to produce a compound of formula

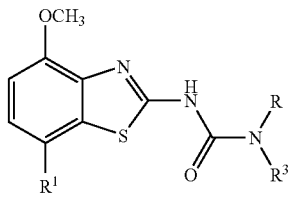

Ic wherein
R$^1$ is selected from 1,4-dioxepanyl and tetrahydropyran-4-yl;
R$^2$ is selected from
—N(R)—(CH$_2$)$_n$-5 membered non aromatic heterocycle,
—N(R)—(CH$_2$)$_n$-5 membered non aromatic heterocycle substituted by one or two substituents selected from lower alkyl, (CH$_2$)$_n$—OH and —NR$_2$,
—N(R)—(CH$_2$)$_n$-6 membered non aromatic heterocycle,
—N(R)—(CH$_2$)$_n$-6 membered non aromatic heterocycle substituted by one or two substituents selected from lower alkyl, (CH$_2$)$_n$—OH and —NR$_2$,
—(CH$_2$)$_n$-5 membered non aromatic heterocycle,
—(CH$_2$)$_n$-5 membered non aromatic heterocycle substituted by one or two substituents selected from —(CH$_2$)$_n$—OH, lower alkyl and lower alkoxy,
—(CH$_2$)$_n$-6 membered non aromatic heterocycle,
—(CH$_2$)$_n$-6 membered non aromatic heterocycle substituted by one or two substituents selected from —(CH$_2$)$_n$—OH, lower alkyl and lower alkoxy
—(CH$_2$)$_n$-5 membered aromatic heterocycle,
—(CH$_2$)$_n$-5 membered aromatic heterocycle substituted by one or two substituents selected from the group consisting of lower alkyl, lower alkoxy, halogen, halogen-lower alkyl, —CH$_2$N(R)(CH$_2$)$_2$OCH$_3$, —N(R)(CH$_2$)$_2$OCH$_3$, —CH$_2$-morpholinyl and —CH$_2$-pyrrolidinyl,
—(CH$_2$)$_n$-6 membered aromatic heterocycle,
—(CH$_2$)$_n$-6 membered aromatic heterocycle substituted by one or two substituents selected from the group consisting of lower alkyl, lower alkoxy, halogen, halogen-lower alkyl, —CH$_2$N(R)(CH$_2$)$_2$OCH$_3$, —N(R)(CH$_2$)$_2$OCH$_3$, —CH$_2$-morpholinyl and —(CH$_2$)$_n$-pyrrolidinyl,
(CH$_2$)$_n$-cycloalkyl,
(CH$_2$)$_n$-cycloalkyl substituted by hydroxy,
—N(R)—(CH$_2$)$_n$-cycloalkyl,
—N(R)—(CH$_2$)$_n$-cycloalkyl substituted by a group selected from hydroxy and lower alkyl,
—N(R)—(CH$_2$)$_n$-phenyl,
phenyl,
phenyl substituted by one or two substituents selected from the group consisting of lower alkoxy, halogen, halogen-lower alkyl, lower alkyl, —CH$_2$-pyrrolidin-1-yl, —CH$_2$-morpholinyl, —CH$_2$N(R)(CH$_2$)$_2$OCH$_3$ and —CH$_2$—N(R)C(O)-lower alkyl,
1,4-dioxa-8-aza-spiro[4,5]decane,
2-oxa-5-aza-bicyclo[2.2.1]heptane,
1-oxa-8-aza-spiro[4,5]decane,
—N(R)—(CH$_2$)$_n$-7-oxa-bicyclo[2.2.1]hept-2-yl, and
2-aza-bicyclo[2.2.2]decane;

L is a leaving group selected from the group consisting of halogen, —O-phenyl and O-lower alkyl,
$R^3$ is selected from
  —$(CH_2)_n$-5 membered non aromatic heterocycle,
  —$(CH_2)_n$-5 membered non aromatic heterocycle substituted by one or two substituents selected from the group consisting of lower alkyl or —$NR^2$,
  —$(CH_2)_n$-6 membered non aromatic heterocycle,
  —$(CH_2)_n$- or 6 membered non aromatic heterocycle substituted by one or two substituents selected from the group consisting of lower alkyl or —$NR^2$,
  cycloalkyl,
  cycloalkyl substituted by a substituent selected from hydroxy and lower alkyl and
  7-oxa-bicyclo[2.2.1]hept-2-yl;
R is selected from hydrogen or lower alkyl; and
n is 0 or 1.

13. The process of claim 11, which further comprises converting the compounds obtained into a pharmaceutically acceptable salt.

14. The process of claim 12, which further comprises converting the compounds obtained into a pharmaceutically acceptable salt.

15. A pharmaceutical composition which comprises a compound of formula I

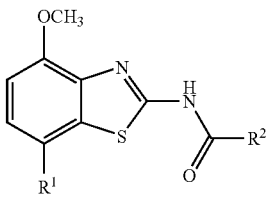

I wherein
  $R^1$ is selected from 1,4-dioxepanyl and tetrahydropyran-4-yl;
  $R^2$ is selected from
    —N(R)—$(CH_2)_n$-5 membered non aromatic heterocycle,
    —N(R)—$(CH_2)_n$-5 membered non aromatic heterocycle substituted by one or two substituents selected from lower alkyl, $(CH_2)_n$—OH and —$NR_2$,
    —N(R)—$(CH_2)_n$-6 membered non aromatic heterocycle,
    —N(R)—$(CH_2)_n$-6 membered non aromatic heterocycle substituted by one or two substituents selected from lower alkyl, $(CH_2)_n$—OH and —$NR_2$,
    —$(CH_2)_n$-5 membered non aromatic heterocycle,
    —$(CH_2)_n$-6 membered non aromatic heterocycle substituted by one or two substituents selected from —$(CH_2)_n$—OH, lower alkyl and lower alkoxy,
    —$(CH_2)_n$-6 membered non aromatic heterocycle,
    —$(CH_2)_n$-6 membered non aromatic heterocycle substituted by one or two substituents selected from —$(CH_2)_n$—OH, lower alkyl and lower alkoxy
    —$(CH_2)_n$-5 membered aromatic heterocycle,
    —$(CH_2)_n$-5 membered aromatic heterocycle substituted by one or two substituents selected from the group consisting of lower alkyl, lower alkoxy, halogen, halogen-lower alkyl, —$CH_2N(R)(CH_2)_2OCH_3$, —$N(R)(CH_2)_2OCH_3$, —$CH_2$-morpholinyl and —$CH_2$-pyrrolidinyl,
    —$(CH_2)_n$-6 membered aromatic heterocycle,
    —$(CH_2)_n$-6 membered aromatic heterocycle substituted by one or two substituents selected from the group consisting of lower alkyl, lower alkoxy, halogen, halogen-lower alkyl, —$CH_2N(R)(CH_2)_2OCH_3$, —$N(R)(CH_2)_2OCH_3$, —$CH_2$-morpholinyl and —$(CH_2)_n$-pyrrolidinyl,
    $(CH_2)_n$-cycloalkyl,
    $(CH_2)_n$-cycloalkyl substituted by hydroxy,
    —N(R)—$(CH_2)_n$-cycloalkyl,
    —N(R)—$(CH_2)_n$-cycloalkyl substituted by a group selected from hydroxy and lower alkyl,
    —N(R)—$(CH_2)_n$-phenyl,
    phenyl,
    phenyl substituted by one or two substituents selected from the group consisting of lower alkoxy, halogen, halogen-lower alkyl, lower alkyl, —$CH_2$-pyrrolidin-1-yl, —$CH_2$-morpholinyl, —$CH_2N(R)(CH_2)_2OCH_3$ and —$CH_2$—N(R)C(O)-lower alkyl,
    1,4-dioxa-8-aza-spiro[4,5]decane,
    2-oxa-5-aza-bicyclo[2.2.1]heptane,
    1-oxa-8-aza-spiro[4,5]decane,
    —N(R)—$(CH_2)_n$-7-oxa-bicyclo[2.2.1]hept-2-yl, and
    2-aza-bicyclo[2.2.2]decane;
R is selected from hydrogen or lower alkyl; and
n is 0 or 1;
or a pharmaceutically acceptable salt thereof,
and a pharmaceutically acceptable carrier.

16. A compound according to claim 1 in which $R^1$ is tetrahydropyran-4-yl and $R^2$ is —N(R)—$(CH_2)_n$-7-oxa-bicyclo[2.2.1]hept-2-yl.

* * * * *